2

United States Patent
Nosaka et al.

(10) Patent No.: US 11,003,079 B2
(45) Date of Patent: May 11, 2021

(54) COMPOSITION FOR FILM FORMATION, FILM, RESIST UNDERLAYER FILM-FORMING METHOD, PRODUCTION METHOD OF PATTERNED SUBSTRATE, AND COMPOUND

(71) Applicant: JSR CORPORATION, Tokyo (JP)

(72) Inventors: Naoya Nosaka, Tokyo (JP); Gouji Wakamatsu, Tokyo (JP); Tsubasa Abe, Tokyo (JP); Yuushi Matsumura, Tokyo (JP); Masayuki Miyake, Tokyo (JP); Yoshio Takimoto, Tokyo (JP)

(73) Assignee: JSR CORPORATION, Tokyo (JP)

( * ) Notice: Subject to any disclaimer, the term of this patent is extended or adjusted under 35 U.S.C. 154(b) by 122 days.

(21) Appl. No.: 16/205,502

(22) Filed: Nov. 30, 2018

(65) Prior Publication Data
US 2019/0094695 A1    Mar. 28, 2019

Related U.S. Application Data

(63) Continuation of application No. PCT/JP2017/018222, filed on May 15, 2017.

(30) Foreign Application Priority Data

Jun. 3, 2016    (JP) .............................. JP2016-112281

(51) Int. Cl.
| G03F 7/00 | (2006.01) |
| G03F 7/11 | (2006.01) |
| G03F 7/26 | (2006.01) |
| G03F 7/09 | (2006.01) |
| C08F 34/02 | (2006.01) |
| C09D 161/12 | (2006.01) |
| C08G 8/20 | (2006.01) |
| C07D 311/74 | (2006.01) |
| C07D 311/92 | (2006.01) |
| C07D 405/14 | (2006.01) |
| C08G 61/10 | (2006.01) |
| C09D 165/00 | (2006.01) |
| H01L 21/027 | (2006.01) |
| C08J 5/18 | (2006.01) |

(52) U.S. Cl.
CPC .............. *G03F 7/11* (2013.01); *C07D 311/74* (2013.01); *C07D 311/92* (2013.01); *C07D 405/14* (2013.01); *C08F 34/02* (2013.01); *C08G 8/20* (2013.01); *C08G 61/10* (2013.01); *C09D 161/12* (2013.01); *C09D 165/00* (2013.01); *G03F 7/094* (2013.01); *G03F 7/26* (2013.01); *H01L 21/0271* (2013.01); *C08G 2261/1422* (2013.01); *C08G 2261/314* (2013.01); *C08J 5/18* (2013.01)

(58) Field of Classification Search
CPC ....................................................... G03F 7/004
See application file for complete search history.

(56) References Cited

U.S. PATENT DOCUMENTS

2005/0074695 A1    4/2005  Nakamura et al.
2017/0184968 A1*   6/2017  Kori ...................... C07C 49/683

FOREIGN PATENT DOCUMENTS

| CN | 103265706 A | * | 8/2013 |
| CN | 103265706 A |   | 8/2013 |
| JP | 5-238990 A |   | 9/1993 |
| JP | 2004-177668 A |   | 6/2004 |
| JP | 2017119671 A |   | 7/2017 |
| WO | WO 200039245 A1 | * | 7/2000 |

OTHER PUBLICATIONS

Y. Morel et al. (Nonlinear absorption spectra of transparent organic crystals for optical limiting applications at visible wavelength, (2000) vol. 115, p. 265-268). (Year: 2000).*
Putala et al. (A chiroptical binaphthopyran switch: amplified CD response in a polystyrene film, New J. Chem., 2010, 34, 1109-1115). (Year: 2010).*
International Search Report dated Jul. 18, 2017 in PCT/JP2017/018222 (with English translation), 5 pages.
Written Opinion of the International Searching Authority dated Jul. 18, 2017 in PCT/JP2017/018222 (with English translation), / pages.
Morel, Y., et al., Nonlinear Absorption Spectra of Transparent Organic Crystals for Optical Limiting Applications at Visible Wavelengths, Synthetic Metals, 2000, vol. 115, pp. 265-268.
Guo, Q., -.S, et al., "A facile synthesis of 3 or 3,3'-substituted binaphthols and their applications in the asymmetric addition of diethylzinc to aldehydes", Journal of Organometallic Chemistry,2006,vol. 691 No. 6, pp. 1282-1287.

(Continued)

*Primary Examiner* — Chanceity N Robinson
(74) *Attorney, Agent, or Firm* — Element IP, PLC

(57) ABSTRACT

The composition for film formation includes a compound including a group of the formula (1) and a solvent. In the formula (1), $R^1$ to $R^4$ each independently represent a hydrogen atom, a monovalent organic group having 1 to 20 carbon atoms, or $R^1$ to $R^4$ taken together represent a cyclic structure having 3 to 20 ring atoms together with the carbon atom or a carbon chain to which $R^1$ to $R^4$ bond. $Ar^1$ represents a group obtained by removing (n+3) hydrogen atoms from an aromatic ring of an arene having 6 to 20 carbon atoms. n is an integer of 0 to 9. $R^5$ represents a hydroxy group, a halogen atom, a nitro group, or a monovalent organic group having 1 to 20 carbon atoms.

(1)

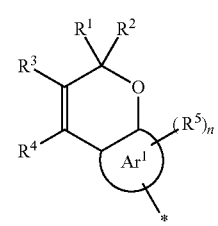

19 Claims, No Drawings

(56) References Cited

OTHER PUBLICATIONS

Badar, Y., et.al., "Optical Activity in the 1,1'-Binaphthyl Series. Optically Active 8,8'-Dimethyl-1,1'-binaphthyl", Journal of the Chemical Society,1965,p. 1412-1418.
Hsieh, J.-C., "O-Dihaloarenes as aryne precursors for nickel-catalyzed [2+2+2] cycloaddition with alkynes and nitriles", Chemical Communications,2008,No. 26, pp. 2992-2994.
Bacon, R.G.R., et al., "Cyclisations with Hydrazine. Part III. Syntheses of Pentaphene and Dinaphtho[2,1-d:1',2'-f][1,2]diazocine", Journal of the Chemical Society,1963,p. 839-845.
Mizoguchi, K., et al., "Negative-Working Photosensitive Poly(phenylene ether) Based on Poly(2,6-dimethyl-1, 4-phenylene ether), a Cross-Linker, and a Photoacid Generator", Macromolecules 2010,vol. 43, pp. 2832-2839.
Mizoguchi, K., et al., "Direct patterning of Poly(ether ether sulfone) Using a Cross-linker and a Photoacid Generator", Polymer Journal, 2008, vol. 40 No. 7, pp. 645-650.
Mizoguchi, K., et al., "Negative-Type Photosensitive Poly(phenylene ether) Based on Poly(2,6-dimethyl-1, 4-phenylene ether), a Crosslinker, and a Photoacid Generator", Journal of Polymer Science: Part A: Polymer Chemistry, vol. 46., 2008, pp. 4949-4958.
Office Action dated Nov. 3, 2020 in Taiwanese Patent Application No. 106117787 (with English translation), 12 pages.
Office Action dated Mar. 2, 2021 in Japanese Patent Application No. 2018-520768 (with English translation), 6 pages.

* cited by examiner

COMPOSITION FOR FILM FORMATION, FILM, RESIST UNDERLAYER FILM-FORMING METHOD, PRODUCTION METHOD OF PATTERNED SUBSTRATE, AND COMPOUND

CROSS-REFERENCE TO RELATED APPLICATIONS

The present application is a continuation application of International Application No. PCT/JP2017/018222, filed May 15, 2017, which claims priority to Japanese Patent Application No. 2016-112281, filed Jun. 3, 2016. The contents of these applications are incorporated herein by reference in their entirety.

BACKGROUND OF THE INVENTION

Field of the Invention

The present invention relates to a composition for film formation, a film, a resist underlayer film-forming method, a production method of a patterned substrate, and a compound.

Discussion of the Background

In manufacturing semiconductor devices, multilayer resist processes have been employed for attaining a high degree of integration. In these processes, a composition for film formation is first applied on the upper face side of a substrate and a film thus obtained is heated to provide a resist underlayer film, and then a resist pattern is formed on the upper face side of the resist underlayer film using a resist composition. Subsequently, the resist underlayer film is etched using the resist pattern as a mask, and further the substrate is etched using the resulting resist underlayer film pattern as a mask to form a desired pattern on the substrate, thereby enabling a patterned substrate to be obtained. Resist underlayer films used in such multilayer resist processes are required to have general characteristics such as solvent resistance and etching resistance.

Recently, patterns are more frequently formed on a substrate having a plurality of types of trenches, in particular trenches having aspect ratios that differ from each other, and the resist underlayer film formed is desired to sufficiently fill these trenches. In this case, a composition for film formation used for forming the resist underlayer film is desired to sufficiently fill these trenches and to be capable of forming a film superior in flatness.

Moreover, the multilayer resist processes involving a procedure of forming a hard mask as an intermediate layer on the resist underlayer film has been studied recently. Specifically, since an inorganic hard mask is formed on a resist underlayer film using a CVD technique according to this procedure, particularly in a case in which a nitride inorganic hard mask is formed, the temperature is elevated to be as high as at least 300° C., and typically no less than 400° C., and thus, the resist underlayer film is required to have superior heat resistance. When heat resistance is insufficient, a component in the resist underlayer film may be sublimated and the sublimated component may adhere to the substrate again, resulting in a disadvantage of decrease in yields of the production of semiconductor devices.

To meet these demands, structures of polymers, etc. contained in the composition for film formation, and functional groups included therein have been extensively investigated (see Japanese Unexamined Patent Application, Publication No. 2004-177668).

SUMMARY OF THE INVENTION

According to one aspect of the present invention, a composition for film formation includes a compound comprising a group represented by formula (1); and a solvent.

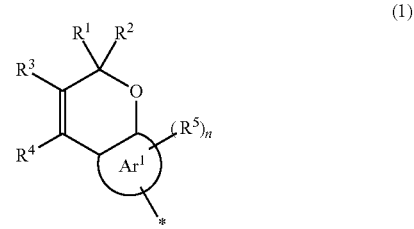

In the formula (1), $R^1$ to $R^4$ each independently represent a hydrogen atom, a monovalent organic group having 1 to 20 carbon atoms, and optionally at least part of $R^1$ to $R^4$ taken together represent a cyclic structure having 3 to 20 ring atoms together with the carbon atom or a carbon chain to which the at least part of $R^1$ to $R^4$ bond. $Ar^1$ represents a group obtained by removing (n+3) hydrogen atoms from an aromatic ring of an arene having 6 to 20 carbon atoms. n is an integer of 0 to 9. $R^5$ represents a hydroxy group, a halogen atom, a nitro group, or a monovalent organic group having 1 to 20 carbon atoms, and optionally in a case in which n is 2 or greater, a plurality of $R^5$s taken together represent a ring structure having 4 to 20 ring atoms together with a carbon chain to which the plurality of $R^5$s bond. In the case in which n is 2 or greater, a plurality of $R^5$s are identical or different. * denotes a binding site to a moiety other than the group represented by the formula (1) in the compound.

According to another aspect of the present invention, a film formed from the composition for film formation.

According to further aspect of the present invention, a resist underlayer film-forming method includes applying the composition for film formation directly or indirectly on an upper face side of a substrate. The film obtained after the applying is heated.

According to further aspect of the present invention, a production method of a patterned substrate includes forming a resist pattern directly or indirectly on an upper face side of a resist underlayer film obtained by the resist underlayer film-forming method. The substrate is etched using the resist pattern as a mask.

According to further aspect of the present invention, a compound includes two or more groups each represented by formula (1).

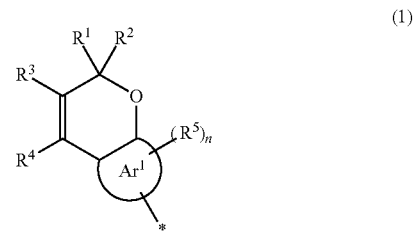

In the formula (1), $R^1$ to $R^4$ each independently represent a hydrogen atom, a monovalent organic group having 1 to 20 carbon atoms, and optionally at least part of $R^1$ to $R^4$ taken together represent a cyclic structure having 3 to 20 ring atoms together with the carbon atom or a carbon chain to which the at least part of $R^1$ to $R^4$ bond. $Ar^1$ represents a group obtained by removing (n+3) hydrogen atoms from an aromatic ring of an arene having 6 to 20 carbon atoms. n is an integer of 0 to 9. $R^5$ represents a hydroxy group, a halogen atom, a nitro group, or a monovalent organic group having 1 to 20 carbon atoms, and optionally in a case in which n is 2 or greater, a plurality of $R^5$s taken together represent a ring structure having 4 to 20 ring atoms together with a carbon chain to which the plurality of $R^5$s bond. In the case in which n is 2 or greater, a plurality of $R^5$s are identical or different. * denotes a binding site to a moiety other than the group represented by the formula (1) in the compound.

DESCRIPTION OF EMBODIMENTS

According to an embodiment of the invention, a composition for film formation contains: a compound (hereinafter, may be also referred to as "(A) compound" or "compound (A)") comprising a group represented by the following formula (1) (hereinafter, may be also referred to as "group (I)"):

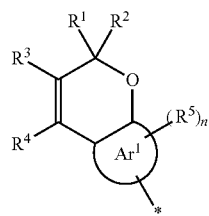

(1)

wherein in the formula (1), $R^1$ to $R^4$ each independently represent a hydrogen atom, a monovalent organic group having 1 to 20 carbon atoms, or $R^1$ to $R^4$ taken together represent a cyclic structure having 3 to 20 ring atoms together with the carbon atom or a carbon chain to which $R^1$ to $R^4$ bond, $Ar^1$ represents a group obtained by removing (n+3) hydrogen atoms from an aromatic ring of an arene having 6 to 20 carbon atoms, $R^5$ represents a hydroxy group, a halogen atom, a nitro group, or a monovalent organic group having 1 to 20 carbon atoms, n is an integer of 0 to 9, wherein, in a case in which n is 2 or greater, a plurality of $R^5$s may be identical or different, or the plurality of $R^5$s taken together represent a ring structure having 4 to 20 ring atoms together with a carbon chain to which the plurality of $R^5$s bond, and * denotes a binding site to a moiety other than the group (I) in the compound (A); and a solvent (hereinafter, may be also referred to as "(B) solvent" or "solvent (B)").

According to another embodiment of the invention, a film is formed from the composition for film formation according to the above embodiment of the present invention.

According to yet another embodiment of the invention, a resist underlayer film-forming method includes: applying the composition for film formation directly or indirectly on an upper face side of a substrate; and heating a film obtained after the applying.

According to still another embodiment of the invention, a production method of a patterned substrate includes: the resist underlayer film-forming method according to the yet another embodiment; forming a resist pattern directly or indirectly on an upper face side of a resist underlayer film obtained by the resist underlayer film-forming method; and etching using the resist pattern as a mask.

According to still yet another embodiment of the invention, a compound includes two or more groups (I).

The composition for film formation according to the embodiment of the present invention is capable of forming a film that is superior in flatness, solvent resistance, etching resistance and heat resistance. The film according to the another embodiment of the present invention is superior in flatness, solvent resistance, etching resistance and heat resistance. The resist underlayer film-forming method of the still another embodiment of the present invention enables formation of a resist underlayer film superior in flatness. The method for producing a patterned substrate according to the yet another embodiment of the present invention enables a substrate having a favorable pattern configuration to be obtained using the superior resist underlayer film thus formed. The compound according to the still yet another embodiment of the present invention can be suitably used as a component for the composition for film formation. Therefore, these can be suitably used in manufacture of semiconductor devices, and the like in which further progress of miniaturization is expected in the future.

DESCRIPTION OF EMBODIMENTS

Composition for Film Formation

The composition for film formation according to an embodiment of the present invention contains the compound (A) and the solvent (B). The composition for film formation may contain an acid generating agent (hereinafter, may be also referred to as "(C) acid generating agent" or "acid generating agent (C)") and/or a crosslinking agent (hereinafter, may be also referred to as "(D) crosslinking agent" or "crosslinking agent (D)") as a favorable component, and may contain other optional component within a range not leading to impairment of the effects of the present invention. Hereinafter, each component is explained.

(A) Compound

The compound (A) includes the group (I). The compound (A) may include either one group (I), or two or more groups (I). Either one type, or two or more types of the compound (A) may be used.

Due to the compound (A) including the group (I), the composition for film formation is capable of forming a film that is superior in flatness, solvent resistance, etching resistance and heat resistance. Although not necessarily clarified and without wishing to be bound by any theory, the reason for achieving the effects described above due to the composition for film formation having the aforementioned constitution is inferred as in the following, for example. Specifically, the group (I) has a structure (chromene structure) constituted of an aromatic ring of $Ar^1$ in the formula (1) and —O—C—C=C— bonding to the aromatic ring. In the compound (A), crosslinking between molecules is enabled by way of —O—C—C=C—, and consequently contraction in volume during the crosslinking would be small. Accordingly, the flatness of the film formed from the composition for film formation is believed to be improved. In addition, due to the compound (A) including $Ar^1$ in the group (I), a proportion of the aromatic ring is great even after the crosslinking, and consequently solvent resistance, etching resistance, and heat resistance of the film to be formed are believed to be improved.

Group (I)

The group (I) is represented by the following formula (1).

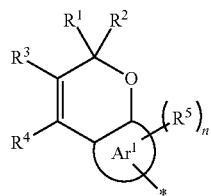

(1)

In the formula (1), $R^1$ to $R^4$ each independently represent a hydrogen atom, a monovalent organic group having 1 to 20 carbon atoms, or $R^1$ to $R^4$ taken together represent a cyclic structure having 3 to 20 ring atoms together with the carbon atom or a carbon chain to which $R^1$ to $R^4$ bond; $Ar^1$ represents a group obtained by removing (n+3) hydrogen atoms from an aromatic ring of an arene having 6 to 20 carbon atoms; $R^5$ represents a hydroxy group, a halogen atom, a nitro group, or a monovalent organic group having 1 to 20 carbon atoms; n is an integer of 0 to 9, wherein, in a case in which n is 2 or greater, a plurality of $R^5$s may be identical or different, or the plurality of $R^5$s taken together represent a ring structure having 4 to 20 ring atoms together with a carbon chain to which the plurality of $R^5$s bond; and * denotes a binding site to a moiety other than the group (I) in the compound (A).

The monovalent organic group having 1 to 20 carbon atoms which may be represented by $R^1$ to $R^4$ is exemplified by: a monovalent hydrocarbon group having 1 to 20 carbon atoms; a group (a) that includes a divalent hetero atom-containing group between two adjacent carbon atoms of the hydrocarbon group or between the hydrocarbon group and a carbon atom to which $R^1$ to $R^4$ bond; a group obtained from the monovalent hydrocarbon group or the group (a) by substituting with a monovalent hetero atom-containing group a part or all of hydrogen atoms included therein; and the like.

Examples of the monovalent hydrocarbon group having 1 to 20 carbon atoms include chain hydrocarbon groups such as:

an alkyl group, e.g., a methyl group, an ethyl group, a propyl group, a butyl group, and a pentyl group;

an alkenyl group, e.g., an ethenyl group, a propenyl group and a butenyl group;

an alkynyl group, e.g., an ethynyl group, a propynyl group and a butynyl group; and the like, alicyclic hydrocarbon groups such as:

a cycloalkyl group, e.g., a cyclopentyl group and a cyclohexyl group;

a cycloalkenyl group, e.g., a cyclopropenyl group, a cyclopentenyl group and a cyclohexenyl group;

a bridged cyclic hydrocarbon group, e.g., a norbornyl group and an adamantyl group; and the like, and aromatic hydrocarbon groups such as:

an aryl group, e.g., a phenyl group, a tolyl group, a xylyl group and a naphthyl group;

an aralkyl group, e.g., a benzyl group, a phenethyl group and a naphthylmethyl group; and the like. Of these, the aromatic hydrocarbon groups are preferred, the aryl group is more preferred, and the phenyl group is still more preferred.

Examples of the divalent hetero atom-containing group include —CO—, —CS—, —NH—, —O—, —S—, groups obtained by combining the same, and the like.

Examples of the group (a) that includes a divalent hetero atom-containing group between two adjacent carbon atoms of the hydrocarbon group or between the hydrocarbon group and a carbon atom to which $R^1$ to $R^4$ bond include:

hetero atom-containing groups such as an oxoalkyl group, a thioalkyl group, an alkylaminoalkyl group, an alkoxyalkyl group and an alkylthioalkyl group;

aliphatic heterocyclic groups such as an oxocycloalkyl group, a thiocycloalkyl group, an azacycloalkyl group, an oxacycloalkyl group, a thiacycloalkyl group, an oxocycloalkenyl group and an oxathiacycloalkyl group;

aromatic heterocyclic groups such as a heteroaryl group, e.g., a pyrrolyl group, a pyridyl group, a quinolyl group, an isoquinolyl group, a furyl group, a pyranyl group, a thienyl group and a benzothiophenyl group; and the like.

Examples of the monovalent hetero atom-containing group include a hydroxy group, a sulfanyl group, a cyano group, a nitro group, a halogen atom, and the like.

$R^1$ and $R^2$ each represent preferably a hydrogen atom, a substituted or unsubstituted aromatic hydrocarbon group, or a substituted or unsubstituted aromatic heterocyclic group, more preferably the substituted or unsubstituted aromatic hydrocarbon group, or the substituted or unsubstituted aromatic heterocyclic group, still more preferably a substituted or unsubstituted aryl group, or a substituted or unsubstituted heteroaryl group, particularly preferably an aryl group, and more particularly preferably a phenyl group.

$R^3$ represents preferably a hydrogen atom.

$R^4$ represents preferably a hydrogen atom, a substituted or unsubstituted aromatic hydrocarbon group, or a substituted or unsubstituted aromatic heterocyclic group, more preferably a hydrogen atom, a substituted or unsubstituted aryl group, or a substituted or unsubstituted heteroaryl group, still more preferably a hydrogen atom or an aryl group, and particularly preferably a hydrogen atom or a phenyl group.

Examples of the cyclic structure having 3 to 20 ring atoms together with the carbon atom or a carbon chain to which $R^1$ to $R^4$ bond, which may be represented by $R^1$ to $R^4$ taken together, include: alicyclic structures such as a cyclopentane structure, a cyclohexane structure, a cyclooctane structure, a norbornane structure and an adamantane structure; aromatic ring structures such as a fluorene structure and a tetrahydroanthracene structure; and the like. Of these, the aromatic ring structures are preferred, and the fluorene structure is more preferred.

Examples of the arene having 6 to 20 carbon atoms that gives $Ar^1$ include benzene, naphthalene, anthracene, phenanthrene, tetracene, pyrene, triphenylene, and the like. Of these, benzene and naphthalene are preferred.

$R^5$ represents preferably a hydroxy group, a halogen atom or a monovalent organic group having 1 to 20 carbon atoms, more preferably a monovalent hydrocarbon group, and still more preferably an alkyl group.

n is preferably 0 to 3, more preferably 0 to 2, still more preferably 0 or 1, and particularly preferably 0.

Examples of the ring structure having 4 to 20 ring atoms together with a carbon chain to which the plurality of $R^5$s bond, which may be represented by the plurality of $R^5$s taken together, include: alicyclic structures such as a cyclohexane structure; aliphatic heterocyclic structures such as an oxacyclohexane structure; aromatic heterocyclic structures such as a pyridine structure; and the like.

In the case in which $Ar^1$ represents a group derived from benzene, a position of —O— of the phenol structure with respect to the binding site in the group (I) denoted by * in the formula (1) may be any of a para position, a meta position, and an ortho position, and is preferably a para position in light of ease in synthesis of the compound (A). Alternatively, in the case in which $Ar^1$ represents a group derived from naphthalene, and the binding site denoted by * in the formula (1) is the 2-position of the naphthalene ring, a position of —O— of the phenol structure is preferably the 6-position of the naphthalene ring.

In the case in which the group (I) in the compound (A) is, for example, a group represented by the following formula (1'), in which $R^3$ in the above formula (1) represents a hydrogen atom, the group (I) may be formed by reacting a group represented by the following formula (a) (hereinafter, may be also referred to as "group (a)"), with an alcohol compound having a carbon-carbon triple bond represented by the following formula (b) (hereinafter, may be also referred to as "compound (b)") in a solvent such as dichloroethane or chlorobenzene, in the presence of a dehydrating agent such as trimethyl orthoformate, and a catalyst such as pyridinium p-toluenesulfonate or p-toluenesulfonate. In this case, a ring structure (chromene structure) is formed through dehydrative condensation and carbon-carbon bond formation between: an oxygen atom of —OH in a phenol structure ($Ar^1$—OH) included in the group (a) and a carbon atom at an ortho position of an aromatic ring to which —OH bonds; and —OH included in the compound (b) and a carbon atom constituting the carbon-carbon triple bond. The compound (A) can thus be readily synthesized from a compound having a phenol structure.

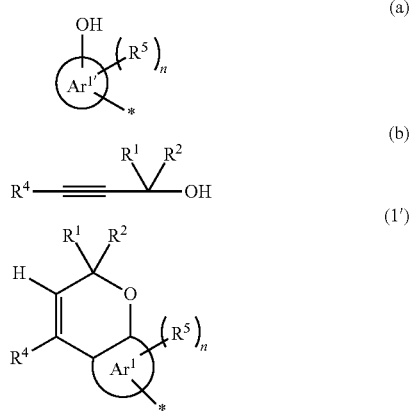

In the formulae (a), (b) and (1'), $R^1$, $R^2$ and $R^4$ each independently represent a hydrogen atom, a monovalent organic group having 1 to 20 carbon atoms, or $R^1$, $R^2$ and $R^4$ taken together represent a cyclic structure having 3 to 20 ring atoms together with the carbon atom or a carbon chain to which $R^1$, $R^2$ and $R^4$ bond; $Ar^{1'}$. represents a group obtained by removing (n+2) hydrogen atoms from an aromatic ring of an arene having 6 to 20 carbon atoms; $R^5$ represents a hydroxy group, a halogen atom, a nitro group, or a monovalent organic group having 1 to 20 carbon atoms; n is an integer of 0 to 9, wherein, in a case in which n is 2 or greater, a plurality of $R^5$s may be identical or different, or the plurality of $R^5$s taken together represent a ring structure having 4 to 20 ring atoms together with a carbon chain to which the plurality of $R^5$s bond; $Ar^1$ represents a group obtained by removing (n+3) hydrogen atoms from an aromatic ring of an arene having 6 to 20 carbon atoms; and * denotes a binding site to a moiety other than the group represented by the formula (a) or the formula (1') in the compound (A).

The lower limit of the number of the groups (I) included in the compound (A) is preferably 2 and more preferably 3. The upper limit of the number is preferably 6, and more preferably 5. When the number of the groups (I) included in the compound (A) falls within the above range, a degree of crosslinking in the film to be formed is increased, resulting in further improvements in the flatness, the solvent resistance, the etching resistance and the heat resistance of the film formed from the composition for film formation.

The compound (A) is exemplified by an aromatic ring-containing compound having a molecular weight of no less than 100 and no greater than 3,000 (hereinafter, may be also referred to as "aromatic ring-containing compound (I)"); a resin (hereinafter, may be also referred to as "resin (I)"); and the like. The term "resin" as referred to means a polymer. The term "aromatic ring-containing compound" as referred to means a compound, which is not a polymer, including an aromatic ring. The aromatic ring-containing compound (I) and the resin (I) will be described hereinafter in this order.

Aromatic Ring-Containing Compound (I)

The aromatic ring-containing compound (I) includes the group (I) and an aromatic ring, and has a molecular weight of no less than 100 and no greater than 3,000. In a case in which the aromatic ring-containing compound (I) has molecular weight distribution, the molecular weight of the aromatic ring-containing compound (I) is a polystyrene equivalent weight average molecular weight (Mw) as determined by gel permeation chromatography (GPC), for example.

The aromatic ring-containing compound (I) preferably includes two or more groups (I). Exemplary aromatic ring-containing compound (I) including two or more groups (I) is a compound represented by the following formula (i), and the like.

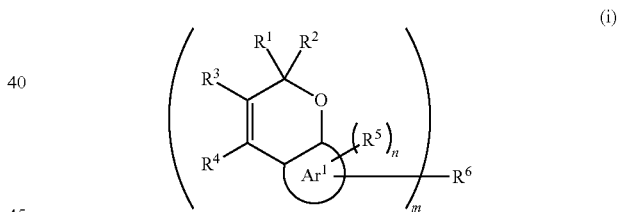

In the above formula (i), $R^1$ to $R^5$, n and $Ar^1$ are as defined in the above formula (1). $R^6$ represents an organic group having a valency of m and 1 to 30 carbon atoms; and m is an integer of 2 to 10, wherein a plurality of R's may be identical or different, a plurality of $R^2$s may be identical or different, a plurality of $R^3$s may be identical or different, a plurality of $R^4$s may be identical or different, in a case in which $R^5$ is present in a plurality of number, a plurality of $R^5$s may be identical or different, or two or more of the plurality of $R^5$s may taken together represent a cyclic structure having 6 to 20 ring atoms together with an atomic chain to which the two or more of the plurality of $R^5$s bond, and $R^6$ and at least one $R^5$ may taken together represent a cyclic structure having 4 to 20 ring atoms together with a carbon chain to which $R^6$ and the at least one $R^5$ bond.

The cyclic structure having 6 to 20 ring atoms which may be represented by the two or more of the plurality of $R^5$s taken together, together with an atomic chain to which the two or more of the plurality of $R^5$s bond, is exemplified by: alicyclic structures such as a cyclohexane structure and a cyclohexene structure; aliphatic heterocyclic structures such as an azacyclohexane structure and an azacyclohexene structure; aromatic heterocyclic structures such as a pyridine structure; and the like.

The cyclic structure having 4 to 20 ring atoms which may be represented by $R^6$ and at least one $R^5$ taken together, together with a carbon chain to which $R^6$ and the at least one $R^5$ bond is exemplified by a hydrocarbon ring structure, a heterocyclic structure, and the like.

The organic group represented by $R^6$ is exemplified by a substituted or unsubstituted hydrocarbon group, a substituted or unsubstituted heterocyclic group, and the like, and specifically by the groups represented by the following formulae (2-1) to (2-5) (hereinafter, may be also referred to as "groups (2-1) to (2-5)") and the like.

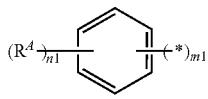

(2-1)

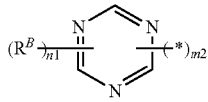

(2-2)

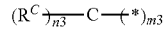

(2-3)

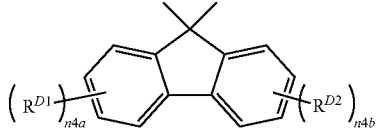

(2-4)

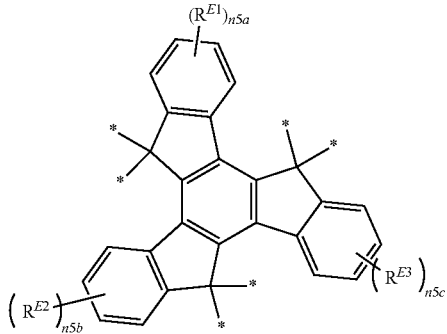

(2-5)

In the above formulae (2-1) to (2-5), * denotes a binding site to the carbon atom in the aromatic ring of $Ar^1$ in the above formula (i).

In the above formula (2-1), $R^A$ represents a hydroxy group, a halogen atom, a nitro group, or a monovalent organic group having 1 to 20 carbon atoms; n1 is an integer of 0 to 4, wherein in a case in which n1 is 2 or greater, a plurality of $R^A$s may be identical or different; and m1 is an integer of 2 to 6, wherein n1+m1≤6.

In the above formula (2-2), $R^B$ represents a hydroxy group, a halogen atom, a nitro group, or a monovalent organic group having 1 to 20 carbon atoms; n2 is an integer of 0 or 1; and m2 is an integer of 2 or 3, wherein n2+m2≤3.

In the above formula (2-3), $R^C$ represents a hydrogen atom, a hydroxy group, a halogen atom, a nitro group, or a monovalent organic group having 1 to 20 carbon atoms; n3 is an integer of 0 to 2, wherein in a case in which n3 is 2, a plurality of $R^C$s may be identical or different; and m3 is an integer of 2 to 4, wherein n3+m3=4.

In the above formula (2-4), $R^{D1}$ and $R^{D2}$ each independently represent a hydroxy group, a halogen atom, a nitro group, or a monovalent organic group having 1 to 20 carbon atoms; and n4a and n4b are each independently an integer of 0 to 4, wherein in a case in which n4a is 2 or greater, a plurality of $R^{D1}$s may be identical or different, and in a case in which n4b 2 or greater, a plurality of $R^{D2}$s may be identical or different.

In the above formula (2-5), $R^{E1}$ to $R^{E3}$ each independently represent a hydroxy group, a halogen atom, a nitro group, or a monovalent organic group having 1 to 20 carbon atoms; and n5a, n5b and n5c are each independently an integer of 0 to 4, wherein in a case in which n5a is 2 or greater, a plurality of $R^{E1}$s may be identical or different, in a case in which n5b 2 or greater, a plurality of $R^{E2}$s may be identical or different, and in a case in which n5c 2 or greater, a plurality of $R^{E3}$s may be identical or different.

In the group (2-1), $R^A$ represents preferably a hydroxy group, a halogen atom, or a monovalent hydrocarbon group. Preferably, n1 is 0 or 1, and more preferably 0. Preferably, m1 is 2, 3, 4 or 6, and more preferably 3.

In the group (2-2), $R^B$ represents preferably a hydroxy group, a halogen atom, or a monovalent hydrocarbon group. Preferably, n2 is 0. Preferably, m2 is 3.

In the group (2-3), $R^C$ represents preferably a hydrogen atom or a monovalent hydrocarbon group, more preferably a hydrogen atom, an alkyl group or an aryl group, and still more preferably a hydrogen atom, a methyl group, an ethyl group, a phenyl group or a biphenyl group. Preferably, n3 is 2 or 3.

In the group (2-4), $R^{D1}$ and $R^{D2}$ each represent preferably a hydroxy group, a halogen atom or a monovalent hydrocarbon group. Preferably, n4a and n4b are each 0 or 1, and more preferably 0.

In the group (2-5), $R^{E1}$ to $R^{E3}$ each represent preferably a hydroxy group, a halogen atom or a monovalent hydrocarbon group. Preferably, n5a, n5b and n5c are each 0 or 1, and more preferably 0.

$R^6$ represents preferably the group (2-1), the group (2-2), the group (2-3) or the group (2-4).

Examples of the aromatic ring-containing compound (I) include compounds represented by the following formulae (i-1) to (i-8) (hereinafter, may be also referred to as "compounds (i-1) to (i-8)"), and the like.

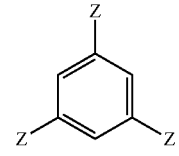

(i-1)

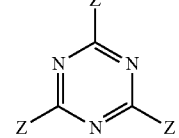

(i-2)

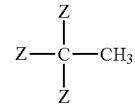

(i-3)

-continued

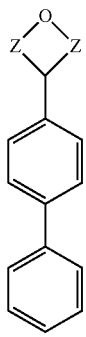
(i-4)

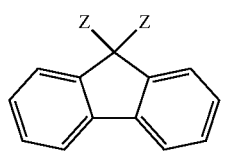
(i-5)

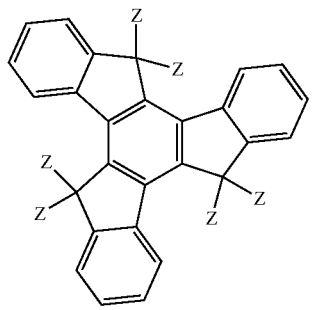
(i-6)

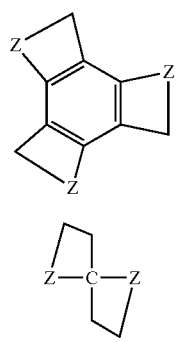
(i-7)

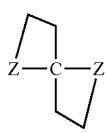
(i-8)

In the above formulae (i-1) to (i-8), Z each independently represents the group (I).

The aromatic ring-containing compound (I) is preferably the compounds (i-1), (i-2), (i-3), (i-4) and (i-5), and more preferably the compounds (i-1), (i-2), (i-3) and (i-5).

The lower limit of the molecular weight of the aromatic ring-containing compound (I) is preferably 300, more preferably 400, still more preferably 500, and particularly preferably 600. The upper limit of the molecular weight is preferably 2,000, more preferably 1,500, and still more preferably 1,300. When the molecular weight of the aromatic ring-containing compound (I) falls within the above range, more improvement of the flatness of the film is enabled.

Resin (I)

The resin (I) includes the group (I). The resin (I) is exemplified by a resin including an aromatic ring in a main chain thereof, a resin including an aromatic ring in a side chain thereof with no aromatic ring in the main chain, and the like. The term "main chain" as referred to means the longest one of the chains constituted of atoms in the compound (A). The term "side chain" as referred to means a chain constituted of atoms in the compound (A) other than the longest one. The resin (I) is typically a compound including a plurality of groups (I).

The resin (I) may be a polycondensation compound, a compound obtained by a reaction other than polycondensation, or the like.

Examples of the resin (I) include a phenol resin, a naphthol resin, a fluorene resin, a styrene resin, an acenaphthylene resin, an indene resin, a polyarylene resin, a triazine resin, a pyrene resin, a fullerene resin, a calixarene resin, and the like.

Phenol Resin

The phenol resin has a structural unit derived from a phenol compound, the structural unit including the group (I). The phenol resin is obtained by reacting the phenol compound with an aldehyde compound by using an acid catalyst or an alkaline catalyst.

The phenol compound is exemplified by phenol, cresol, xylenol, resorcinol, bisphenol A, p-tert-butylphenol, p-octylphenol, and the like.

The aldehyde compound is exemplified by: aldehydes such as formaldehyde; aldehyde sources such as paraformaldehyde and trioxane; and the like.

Naphthol Resin

The naphthol resin has a structural unit derived from a naphthol compound, the structural unit including the group (I). The naphthol resin is obtained by reacting the naphthol compound with the aldehyde compound by using an acid catalyst or an alkaline catalyst.

The naphthol compound is exemplified by α-naphthol, β-naphthol, 1,5-dihydroxynaphthalene, 2,7-dihydroxynaphthalene, and the like.

Fluorene Resin

The fluorene resin has a structural unit derived from a fluorene compound, the structural unit including the group (I). The fluorene resin is obtained by reacting the fluorene compound with the aldehyde compound by using an acid catalyst or an alkaline catalyst.

The fluorene compound is exemplified by 9,9-bis(4-hydroxyphenyl)fluorene, 9,9-bis(4-hydroxyphenyl)fluorene, 9,9-bis(6-hydroxynaphthyl)fluorene, and the like.

Styrene Resin

The styrene resin has a structural unit derived from a compound having an aromatic ring and a polymerizable carbon-carbon double bond, the structural unit including the group (I). The styrene resin can be synthesized by, for example, forming the group (I) from a phenol structure of a resin having the structural unit derived from the compound having: an aromatic ring including a phenolic hydroxyl group; and a polymerizable carbon-carbon double bond.

Acenaphthylene Resin

The acenaphthylene resin has a structural unit derived from an acenaphthylene compound, the structural unit including the group (I). The acenaphthylene resin can be synthesized by, for example, forming the group (I) from a phenol structure of a resin having the structural unit derived from an acenaphthylene compound including a phenolic hydroxyl group.

Indene Resin

The indene resin has a structural unit derived from an indene compound, the structural unit including the group (I). The indene resin can be synthesized by, for example, forming the group (I) from a phenol structure of a resin having the structural unit derived from an indene compound including a phenolic hydroxyl group.

Arylene Resin

The arylene resin has an arylene skeleton including the group (I). The arylene resin can be synthesized by, for example, forming the group (I) from a phenol structure of a resin having an arylene skeleton including a phenolic hydroxyl group. The arylene skeleton is exemplified by a phenylene skeleton, a naphthylene skeleton, a biphenylene skeleton, and the like.

Triazine Resin

The triazine resin has a triazine skeleton including the group (I). The triazine resin can be synthesized by, for example, forming the group (I) from a phenol structure of a resin having a triazine skeleton including a phenolic hydroxyl group.

Pyrene Resin

The pyrene resin has a pyrene skeleton including the group (I). The pyrene resin can be synthesized by, for example, forming the group (I) from a phenol structure of a resin having a pyrene skeleton including a phenolic hydroxyl group. The resin having a pyrene skeleton including a phenolic hydroxyl group is, for example, a resin obtained by reacting a pyrene compound including a phenolic hydroxyl group with the aldehyde compound by using an acid catalyst.

Fullerene Resin

The fullerene resin has a fullerene skeleton including the group (I). The fullerene resin can be synthesized by, for example, forming the group (I) from a phenol structure of a resin having a fullerene skeleton including a phenolic hydroxyl group.

In the case in which the compound (A) is the phenol resin, the naphthol resin, the fluorene resin, the styrene resin, the acenaphthylene resin, the indene resin, the arylene resin, the triazine resin, the pyrene resin or the fullerene resin, the lower limit of Mw of the compound (A) is preferably 500 and more preferably 1,000. Meanwhile, the upper limit of Mw is preferably 50,000, more preferably 10,000, and still more preferably 8,000.

The lower limit of Mw/Mn of the compound (A) is typically 1, and preferably 1.1. The upper limit of Mw/Mn is preferably 5, more preferably 3, and still more preferably 2.

When Mw and Mw/Mn of the compound (A) fall within the above range, more improvement of the flatness and surface coating characteristics of the film formed from the composition for film formation is enabled.

Calixarene Resin

The calixarene resin is a cyclic oligomer including the group (I) in which a plurality of aromatic rings, each having a phenolic hydroxyl group bonded thereto, circularly bond to each other via hydrocarbon groups. The calixarene resin including the group (I) can be synthesized by, for example, forming the group (I) from a phenol structure of a calixarene resin.

In the case in which the compound (A) is the calixarene resin, the lower limit of a molecular weight of the calixarene resin is preferably 500, more preferably 700, and still more preferably 1,000 in light of more improvement of the flatness of the film formed from the composition for film formation. The upper limit of the molecular weight is preferably 5,000, more preferably 3,000, and still more preferably 1,500.

The lower limit of the content of the compound (A) with respect to the total solid content in the composition for film formation is preferably 70% by mass, more preferably 80% by mass, and still more preferably 85% by mass. Meanwhile, the upper limit of the content is, for example, 100% by mass. The "total solid content" as referred to means the sum of the components other than the solvent (B) in the composition for film formation.

The lower limit of the content of the compound (A) in the composition for film formation is preferably 1% by mass, more preferably 3% by mass, and still more preferably 5% by mass. The upper limit of the content is preferably 50% by mass, more preferably 30% by mass, and still more preferably 15% by mass.

(B) Solvent

The solvent (B) is not particularly limited as long as it can dissolve or disperse the compound (A), and the optional component contained as needed.

The solvent (B) is exemplified by an alcohol solvent, a ketone solvent, an ether solvent, an ester solvent, a nitrogen-containing solvent, and the like. The solvent (B) may be used either alone of one type, or in combination of two or more types thereof.

Examples of the alcohol solvent include: monoalcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenyl methyl carbinol, diacetone alcohol and cresol; polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol and glycerin; and the like.

Examples of the ketone solvent include acetone, methyl ethyl ketone, methyl n-propyl ketone, methyl n-butyl ketone, diethyl ketone, methyl iso-butyl ketone, methyl-n-pentyl ketone, ethyl n-butyl ketone, methyl n-hexyl ketone, di-iso-butyl ketone, trimethyl nonanone, cyclohexanone, methylcyclohexanone, 2,4-pentanedione, acetonylacetone, diacetone alcohol, acetophenone, fenchone, and the like.

Examples of the ether solvent include ethyl ether, isopropyl ether, n-butyl ether, n-hexyl ether, 2-ethyl hexyl ether, ethylene oxide, 1,2-propylene oxide, dioxolane, 4-methyl dioxolane, dioxane, dimethyl dioxane, 2-methoxyethanol, 2-ethoxyethanol, ethylene glycol diethyl ether, 2-n-butoxyethanol, 2-n-hexoxyethanol, 2-phenoxyethanol, 2-(2-ethylbutoxy)ethanol, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxytriglycol, tetraethylene glycol di-n-butyl ether, 1-n-butoxy-2-propanol, 1-phenoxy-2-propanol, propylene glycol monomethyl ether, propylene glycol monoethyl ether, propylene glycol monopropyl ether, dipropylene glycol monomethyl ether, dipropylene glycol monoethyl ether, dipropylene glycol monopropyl ether, tripropylene glycol monomethyl ether, tetrahydrofuran, 2-methyltetrahydrofuran, and the like.

Examples of the ester solvent include diethyl carbonate, methyl acetate, ethyl acetate, γ-butyrolactone, γ-valerolactone, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methyl cyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the nitrogen-containing solvent include N-methylformamide, N,N-dimethylformamide, N,N-diethylformamide, acetamide, N-methylacetamide, N,N-dimethylacetamide, N-methylpropionamide, N-methylpyrrolidone, and the like.

Of these, the ether solvent and the ester solvent are preferred, and an ether solvent and an ester solvent each having a glycol structure are more preferred in light of superior film formability.

Exemplary ether solvent and exemplary ester solvent each having a glycol structure include propylene glycol monomethyl ether, propylene glycol monoethyl ether, propylene glycol monopropyl ether, propylene glycol monomethyl ether acetate, propylene glycol monoethyl ether acetate, propylene glycol monopropyl ether acetate, and the like. Of these, propylene glycol monomethyl ether acetate is particularly preferred.

The lower limit of the percentage content of the ether solvent and the ester solvent, each having a glycol structure, in the solvent (B) is preferably 20% by mass, more preferably 60% by mass, still more preferably 90% by mass, and particularly preferably 100% by mass.

(C) Acid Generating Agent

The acid generating agent (C) generates an acid by an action of heat and/or light to promote the crosslinking of molecules of the compound (A). When the composition for film formation contains the acid generating agent (C), the crosslinking reaction of molecules of the compound (A) is promoted and consequently the hardness of the formed film is enabled to be further increased. The acid generating agent (C) may be used either alone of one type, or in combination of two or more types thereof.

The acid generating agent (C) is exemplified by an onium salt compound, an N-sulfonyloxyimide compound, and the like.

The onium salt compound is exemplified by a sulfonium salt, a tetrahydrothiophenium salt, an iodonium salt, an ammonium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-bicyclo[2.2.1]hept-2-yl-1,1,2,2-tetrafluoroethanesulfonate, 1-(6-n-butoxynaphthalen-2-yl) tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl) tetrahydrothiophenium perfluoro-n-octanesulfonate, 1-(6-n-butoxynaphthalen-2-yl)tetrahydrothiophenium 2-bicyclo [2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1, 1,2,2-tetrafluoroethanesulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1, 2,2-tetrafluoroethanesulfonate, bis(4-t-butylphenyl) iodonium trifluoromethanesulfonate, bis(4-t-butylphenyl) iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the ammonium salt include triethylammonium trifluoromethane sulfonate, triethylammonium nonafluoro-n-butanesulfonate, trimethylammonium nonafluoro-n-butanesulfonate, tetraethylammonium nonafluoro-n-butanesulfonate, triethylammonium perfluoro-n-octanesulfonate, triethylammonium 2-bicyclo[2.2.1]hept-2-yl-1,1,2,2-tetrafluoroethanesulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy) bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Of these, the acid generating agent (C) is preferably the onium salt compound, more preferably the iodonium salt or the ammonium salt, and still more preferably bis(4-t-butylphenyl)iodonium nonafluoro-n-butanesulfonate or triethylammonium nonafluoro-n-butanesulfonate.

When the composition for film formation contains the acid generating agent (C), the lower limit of the content of the acid generating agent (C) with respect to 100 parts by mass of the compound (A) is preferably 0.1 parts by mass, more preferably 1 part by mass, and still more preferably 3 parts by mass. The upper limit of the content is preferably 20 parts by mass, more preferably 15 parts by mass, and still more preferably 12 parts by mass. When the content of the acid generating agent (C) falls within the above range, the crosslinking reaction of molecules of the compound (A) may be facilitated more effectively.

(D) Crosslinking Agent

The crosslinking agent (D) forms crosslinking bonds between components such as the compound (A) in the composition for film formation, or forms cross-linked structures by molecules of itself, through an action of heat and/or an acid. When the composition for film formation contains the crosslinking agent (D), the hardness of the formed film is enabled to be increased. The crosslinking agent (D) may be used either alone of one type, or in combination of two or more types thereof.

The crosslinking agent (D) is exemplified by a polyfunctional (meth)acrylate compound, an epoxy compound, a hydroxymethyl group-substituted phenol compound, an alkoxyalkyl group-containing phenol compound, a compound having an alkoxyalkylated amino group, a random copolymer of an acenaphthylene with hydroxymethylacenaphthylene which is represented by the following formula (7-P), compounds represented by the following formulae (11-1) to (11-12), and the like.

Examples of the polyfunctional (meth)acrylate compound include trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl)isocyanurate tri(meth)acrylate, ethylene glycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethylene glycol di(meth)acrylate, triethylene glycol di(meth)acrylate, dipropylene glycol di(meth)acrylate, bis(2-hydroxyethyl)isocyanurate di(meth)acrylate, and the like.

Examples of the epoxy compound include novolak epoxy resins, bisphenol epoxy resins, alicyclic epoxy resins, aliphatic epoxy resins, and the like.

Examples of the hydroxymethyl group-substituted phenol compound include 2-hydroxymethyl-4,6-dimethylphenol, 1,3,5-trihydroxymethylbenzene, 3,5-dihydroxymethyl-4-methoxytoluene (i.e., 2,6-bis(hydroxymethyl)-p-cresol), and the like.

Examples of the alkoxyalkyl group-containing phenol compound include methoxymethyl group-containing phenol compounds, ethoxymethyl group-containing phenol compounds, and the like.

Examples of the compound having an alkoxyalkylated amino group include nitrogen-containing compounds having a plurality of active methylol groups in a molecule thereof, wherein the hydrogen atom of the hydroxyl group of at least one of the methylol groups is substituted with an alkyl group such as a methyl group or a butyl group, and the like; examples thereof include (poly)methylolated melamines, (poly)methylolated glycolurils, (poly)methylolated benzoguanamines, (poly)methylolated ureas, and the like. It is to be noted that a mixture constituted with a plurality of substituted compounds described above may be used as the compounds having an alkoxyalkylated amino group, and the compound having an alkoxyalkylated amino group may contain an oligomer component formed through partial self-condensation thereof.

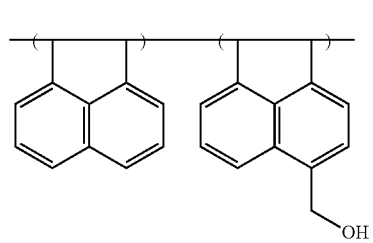

(11-P)

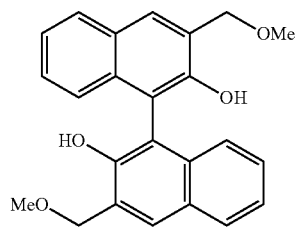

(11-1)

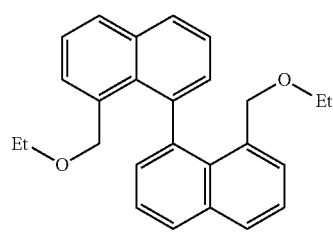

(11-2)

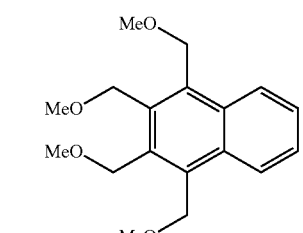

(11-3)

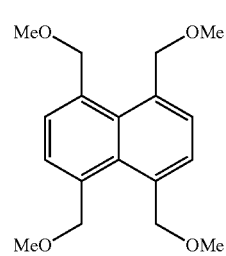

(11-4)

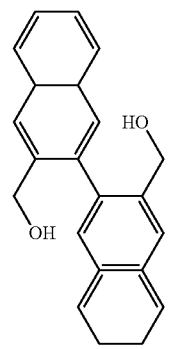

(11-5)

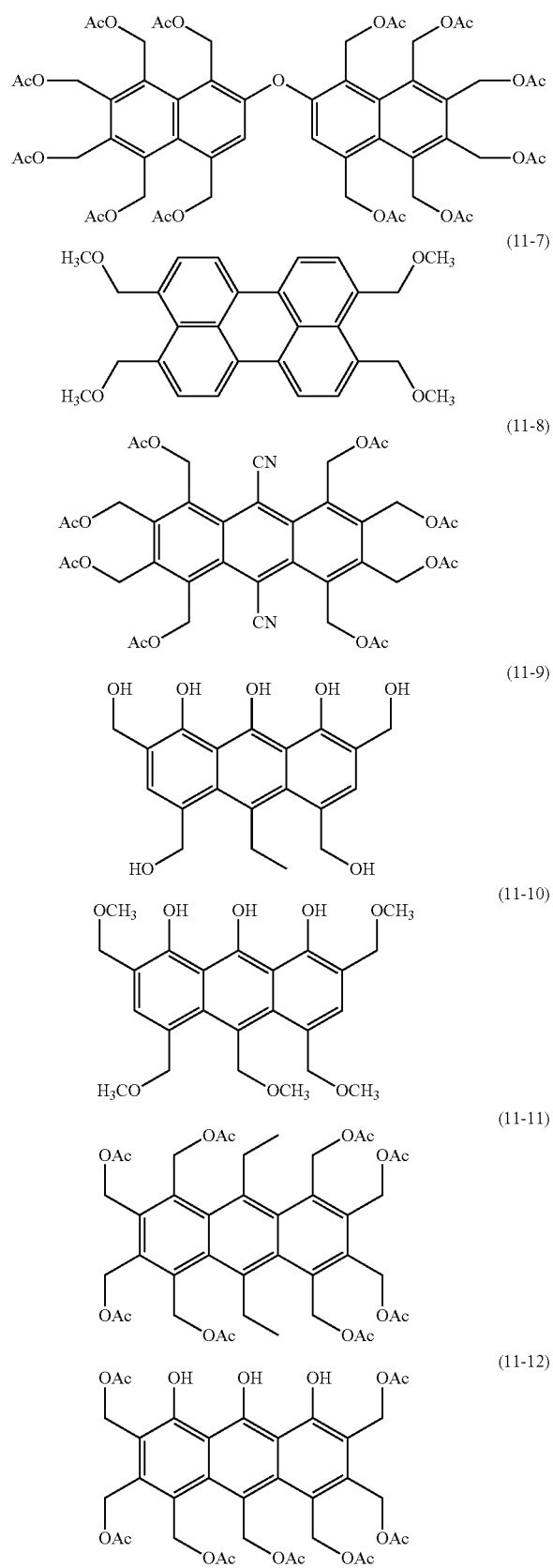

In the above formulae (11-6), (11-8), (11-11) and (11-12), Ac represents an acetyl group.

It is to be noted that the compounds represented by the above formulae (11-1) to (11-12) each may be synthesized with reference to the following documents.

The compound represented by the formula (11-1):
Guo, Qun-Sheng; Lu, Yong-Na; Liu, Bing; Xiao, Jian; and Li, Jin-Shan, Journal of Organometallic Chemistry, 2006, vol. 691, #6, p. 1282-1287.

The compound represented by the formula (11-2):
Badar, Y. et al., Journal of the Chemical Society, 1965, p. 1412-1418.

The compound represented by the formula (11-3):
Hsieh, Jen-Chieh; Cheng, Chien-Hong, Chemical Communications (Cambridge, United Kingdom), 2008, #26, p. 2992-2994.

The compound represented by the formula (11-4):
Japanese Unexamined Patent Application, Publication No. H5-238990.

The compound represented by the formula (11-5):
Bacon, R. G R.; Bankhead, R., Journal of the Chemical Society, 1963, p. 839-845.

The compounds represented by the formulae (11-6), (11-8), (11-11) and (11-12):
Macromolecules, 2010, vol. 43, p. 2832-2839.

The compounds represented by the formulae (11-7), (11-9) and (11-10):
Polymer Journal, 2008, vol. 40, No. 7, p. 645-650; and Journal of Polymer Science: Part A, Polymer Chemistry, vol. 46, p. 4949-4958.

Among these crosslinking agents (D), the methoxymethyl group-containing phenol compound, the compound having an alkoxyalkylated amino group, and the random copolymer of acenaphthylene with hydroxymethylacenaphthylene are preferred, the compound having an alkoxyalkylated amino group is more preferred, and 1,3,4,6-tetra(methoxymethyl) glycoluril is still more preferred.

When the composition for film formation contains the crosslinking agent (D), the lower limit of the content of the crosslinking agent (D) with respect to 100 parts by mass of the compound (A) is preferably 0.1 parts by mass, more preferably 0.5 parts by mass, still more preferably 1 part by mass, and particularly preferably 3 parts by mass. The upper limit of the content is preferably 100 parts by mass, more preferably 50 parts by mass, still more preferably 30 parts by mass, and particularly preferably 20 parts by mass. When the content of the crosslinking agent (D) falls within the above range, the crosslinking reaction of molecules of the compound (A) may be allowed to occur more effectively.

Other Optional Component

Other optional component is exemplified by a surfactant and the like.

Surfactant

When the composition for film formation contains the surfactant, coating characteristics thereof can be improved, and consequently uniformity of the surface of the formed film may be improved and occurrence of the unevenness of coating can be inhibited. The surfactant may be used either alone of one type, or in combination of two or more types thereof.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, and the like. Examples of commercially available surfactant include KP341 (available from Shin-Etsu Chemical Co., Ltd.); Polyflow No. 75 and Polyflow No. 95 (each available from Kyoeisha Chemical Co., Ltd.); EFTOP EF101, EFTOP EF204, EFTOP EF303 and EFTOP EF352 (each available from Tochem Products Co. Ltd.); Megaface F171, Megaface F172 and Megaface F173 (each available from DIC Corporation); Fluorad FC430, Fluorad FC431, Fluorad FC135 and Fluorad FC93 (each available from Sumitomo 3M Limited); ASAHI GUARD AG710, Surflon S382, Surflon SC101, Surflon SC102, Surflon SC103, Surflon SC104, Surflon SC105 and Surflon SC106 (each available from Asahi Glass Co., Ltd.); and the like.

When the composition for film formation contains the surfactant, the lower limit of the content of the surfactant with respect to 100 parts by mass of the compound (A) is preferably 0.01 parts by mass, more preferably 0.05 parts by mass, and still more preferably 0.1 parts by mass. The upper limit of the content is preferably 10 parts by mass, more preferably 5 parts by mass, and still more preferably 1 part by mass. When the content of the surfactant falls within the above range, the coating characteristics of the composition for film formation is enabled to be more improved.

Preparation Procedure of Composition for Film Formation

The composition for film formation may be prepared, for example, by mixing the compound (A) and the solvent (B), as well as the acid generating agent (C) and the other optional component as needed, at a certain ratio, preferably followed by filtering a mixture thus obtained through a membrane filter, etc. having a pore size of about 0.1 µm. The lower limit of the solid content concentration of the composition for film formation is preferably 0.1% by mass, more preferably 1% by mass, still more preferably 3% by mass, and particularly preferably 5% by mass. The upper limit of the solid content concentration of the composition for resist underlayer film formation is preferably 50% by mass, more preferably 30% by mass, still more preferably 20% by mass, and particularly preferably 15% by mass.

The composition for film formation is capable of forming a film superior in flatness, solvent resistance, etching resistance and heat resistance, and can therefore be suitably used for formation of a resist underlayer film in production of a semiconductor device and the like. In addition, the composition for film formation can also be used for formation of a protective film, an insulating film, a colored cured film in a display device and the like.

Film

The film according to another embodiment of the present invention is formed from the composition for film formation according to the embodiment of the present invention. Since the film is formed from the composition for film formation described above, the film is superior in flatness, solvent resistance, etching resistance and heat resistance. Therefore, the film according to the another embodiment of the present invention can be used as, in addition to a resist underlayer film (described later), a protective film, an insulating film, a colored cured film in a display device and the like.

Resist Underlayer Film-Forming Method

The resist underlayer film-forming method according to yet another embodiment includes: applying the aforementioned composition for film formation directly or indirectly on an upper face side of a substrate (hereinafter, may be also referred to as "applying step"); and heating a film obtained after the applying step (hereinafter, may be also referred to as "heating step"). According to the resist underlayer film-forming method in which the aforementioned composition for film formation is used, formation a resist underlayer film that is superior in flatness, solvent resistance, etching resistance and heat resistance is enabled.

Applying Step

In this step, the composition for film formation is applied directly or indirectly on the upper face side of the substrate. Examples of the substrate include a silicon wafer, a wafer coated with aluminum, and the like. The applying procedure of the composition for film formation is not particularly limited, and for example, an appropriate procedure such as spin coating, cast coating and roll coating may be employed to form a coating film.

Heating Step

In this step, the film obtained after the applying step is heated. The resist underlayer film is thus formed.

Heating of the film is typically carried out in an ambient air. The lower limit of a heating temperature is preferably 150° C., more preferably 200° C., and still more preferably 250° C. The upper limit of the heating temperature is preferably 500° C., more preferably 450° C., and still more preferably 400° C. When the heating temperature is less than 150° C., oxidative crosslinking may not sufficiently proceed, and characteristics necessary for use in the resist underlayer film may not be exhibited. The lower limit of the heating time period is preferably 15 sec, more preferably 30 sec, and still more preferably 45 sec. The upper limit of the heating time period is preferably 1,200 sec, more preferably 600 sec, and still more preferably 300 sec.

The film may be preheated at a temperature of no less than 60° C. and no greater than 250° C. before being heated at a temperature of no less than 150° C. and no greater than 500° C. The lower limit of the heating time period in the preheating is preferably 10 sec, and more preferably 30 sec. The upper limit of the heating time period is preferably 300 sec, and more preferably 180 sec. When the preheating is carried out to preliminarily evaporate a solvent and make the film dense, a dehydrogenation reaction during the subsequent heating may efficiently proceed.

It is to be noted that in the resist underlayer film-forming method, the resist underlayer film is formed through the heating of the film; however, in a case in which the composition for film formation contains the acid generating agent (C) and the acid generating agent (C) is a radiation-sensitive acid generating agent, the resist underlayer film may be formed also by hardening the film through a combination of an exposure and heating. The radioactive ray used for the exposure may be appropriately selected from: electromagnetic waves such as visible rays, ultraviolet rays, far ultraviolet rays, X-rays and γ radiations; particle rays such as electron beams, molecular beams and ion beams, and the like in accordance with the type of the acid generating agent (C).

The lower limit of the average thickness of the resist underlayer film formed is preferably 50 nm, more preferably 100 nm, and still more preferably 200 nm. The upper limit of the average thickness of the resist underlayer film formed is preferably 3,000 nm, more preferably 2,000 nm, and still more preferably 500 nm.

Production Method of Patterned Substrate

The production method of a patterned substrate according to still another embodiment includes: forming a resist pattern directly or indirectly on an upper face side of a resist underlayer film obtained by the resist underlayer film-forming method (hereinafter, may be also referred to as "resist pattern-forming step"); and etching using the resist pattern as a mask (hereinafter, may be also referred to as "etching step").

According to the production method of a patterned substrate, since the resist underlayer film that is superior in flatness, solvent resistance, etching resistance and heat resistance obtained by the resist underlayer film-forming method is used, a patterned substrate having a superior pattern configuration is enabled to be obtained.

Before the resist pattern-forming step, the production method of a patterned substrate may include as needed, a step of forming an intermediate layer (intermediate film) on the upper face side of the resist underlayer film. Hereinafter, each step is explained.

Intermediate Layer-Forming Step

In this step, an intermediate layer is formed on the upper face side of the resist underlayer film. The intermediate layer as referred to means a layer having a function that is exhibited or not exhibited by the resist underlayer film and/or the resist film in resist pattern formation in order to further enhance the function exhibited by the resist underlayer film and/or the resist film, or to impart to the resist underlayer film and/or the resist film a function not exhibited thereby. For example, when an antireflective film is provided as the intermediate layer, an antireflecting function of the resist underlayer film may be further enhanced.

The intermediate layer may be formed from an organic compound and/or an inorganic oxide. Examples of the organic compound include commercially available products such as: "DUV-42", "DUV-44", "ARC-28" and "ARC-29" (each available from Brewer Science); "AR-3" and "AR-19" (each available from Lohm and Haas Company); and the like. Examples of the inorganic oxide include commercially available products such as "NFC SOG01", "NFC SOG04" and "NFC SOG080" (each JSR Corporation), and the like. As the inorganic oxide, polysiloxanes, titanium oxides, alumina oxides, tungsten oxides, and the like that are provided through a CVD process may also be used.

The forming procedure of the intermediate layer is not particularly limited, and for example, a coating procedure, a CVD technique, or the like may be employed. Of these, the coating procedure is preferred. In a case in which the coating procedure is employed, the intermediate layer may be successively provided after the resist underlayer film is formed. Moreover, the average thickness of the intermediate layer is appropriately selected in accordance with the function required for the intermediate layer, and the lower limit of the average thickness of the intermediate layer is preferably 10 nm, and more preferably 20 nm. The upper limit of the average thickness of the intermediate layer is preferably 3,000 nm, and more preferably 300 nm.

Resist Pattern-Forming Step

In this step, a resist pattern is formed on the upper face side of the resist underlayer film. In the case in which the intermediate layer-forming step is carried out, a resist pattern is formed on the upper face side of the intermediate layer. This step may be carried out by, for example, using a resist composition.

When the resist composition is used, specifically, the resist film is formed by applying the resist composition such that a resultant resist film has a predetermined thickness and thereafter subjecting the resist composition to prebaking to evaporate the solvent in the coating film.

Examples of the resist composition include a chemically amplified positive or negative resist composition that contains a radiation-sensitive acid generating agent; a positive resist composition containing an alkali-soluble resin and a quinone diazide-based photosensitizing agent; a negative resist containing an alkali-soluble resin and a crosslinking agent; and the like.

The lower limit of the solid content concentration of the resist composition is preferably 0.3% by mass, and more preferably 1% by mass. The upper limit of the solid content concentration of the resist composition is preferably 50% by mass, and more preferably 30% by mass. Moreover, the resist composition is generally used for forming a resist film, for example, after being filtered through a filter with a pore size of 0.2 It is to be noted that a commercially available resist composition may be used as is in this step.

The applying procedure of the resist composition is not particularly limited, and examples thereof include a spin-coating method, and the like. The temperature of the prebaking may be appropriately adjusted in accordance with the type of the resist composition employed and the like; however, the lower limit of the temperature is preferably 30° C., and more preferably 50° C. The upper limit of the aforementioned temperature is preferably 200° C., and more preferably 150° C. The lower limit of a time period for the prebaking is preferably 10 sec, and more preferably 30 sec. The upper limit of the time period for the prebaking is preferably 600 sec, and more preferably 300 sec.

Next, the resist film formed is exposed by selective irradiation with a radioactive ray. The radioactive ray used in the exposure may be appropriately selected from: electromagnetic waves such as visible rays, ultraviolet rays, far ultraviolet rays, X-rays and γ radiations; particle rays such as electron beams, molecular beams and ion beams in accordance with the type of the radiation-sensitive acid generating agent used in the resist composition. Among these, far ultraviolet rays are preferred, and a KrF excimer laser beam (248 nm), and an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm) and extreme ultraviolet rays (EUV; wavelength: 13.5 nm, etc.) are more preferred, and a KrF excimer laser beam, an ArF excimer laser beam and EUV are still more preferred.

Post-baking may be carried out after the exposure for the purpose of improving a resolution, a pattern profile, developability, and the like. The temperature of the post-baking may be appropriately adjusted in accordance with the type of the resist composition employed and the like; however, the lower limit of the temperature is preferably 50° C., and more preferably 70° C. The upper limit of the aforementioned temperature is preferably 200° C., and more preferably 150° C. The lower limit of a time period for the post-baking is preferably 10 sec, and more preferably 30 sec. The upper limit of the time period for the post-baking is preferably 600 sec, and more preferably 300 sec.

Next, the resist film exposed is developed with a developer solution to form a resist pattern. The development may be either a development with an alkali or a development with an organic solvent. In the case of the development with an alkali, examples of the developer solution include an alkaline aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water soluble organic solvent, e.g., an alcohol such as methanol and ethanol, a surfactant, and the like may be added to the alkaline aqueous solution. Alternatively, in the case of the development with an organic solvent, examples of the developer solution include a variety of organic solvents exemplified as the solvent (B) in relation to the composition for film formation described above, and the like.

A predetermined resist pattern is formed by the development with the developer solution, followed by washing and drying.

In carrying out the resist pattern-forming step, without using the resist composition described above, other process may be employed, for example, a nanoimprint method may be adopted, or a directed self-assembling composition may be used.

Etching Step

In this step, etching is carried out with the aforementioned resist pattern as a mask to form a pattern on a substrate. The etching may be carried out once or multiple times. In other words, the etching may be carried out sequentially with patterns obtained by the etching as masks. However, in light of obtaining a pattern with a favorable shape, the etching is preferably carried out multiple times. When the etching is carried out multiple times, in a case in which the intermediate layer is not provided, the resist underlayer film and the substrate are subjected to etching sequentially in this order, whereas in a case in which the intermediate layer is provided, the intermediate layer, the resist underlayer film and the substrate are subjected to etching sequentially in this order. The etching step may be exemplified by dry etching, wet etching, and the like. Of these, in light of achieving a pattern with a more favorable shape, dry etching is preferred. For example, gas plasma such as oxygen plasma and the like may be used as the dry etching. After the dry etching, the substrate having a predetermined pattern can be obtained.

EXAMPLES

Hereinafter, the embodiment of the present invention will be explained in more detail by way of Examples, but the present invention is not in any way limited to these Examples. Measuring methods for various types of physical properties are shown below.

Mw and Mn

In the case in which the compound (A) is a polymer, the Mw and the Mn of the compound (A) were determined by gel permeation chromatography using GPC columns ("G2000 HXL"×2, and "G3000 HXL"×1) available from Tosoh Corporation, a differential refractometer as a detector and mono-dispersed polystyrene as a standard under analytical conditions involving a flow rate of 1.0 mL/min, an elution solvent of tetrahydrofuran and a column temperature of 40° C.

Average Thickness of Film

The average thickness of the film was determined using a spectroscopic ellipsometer ("M2000D" available from J. A. WOOLLAM Co.).

Synthesis of Compound (A)

Compounds represented by the following formulae (A-1) to (A-5) were synthesized by the following procedure.

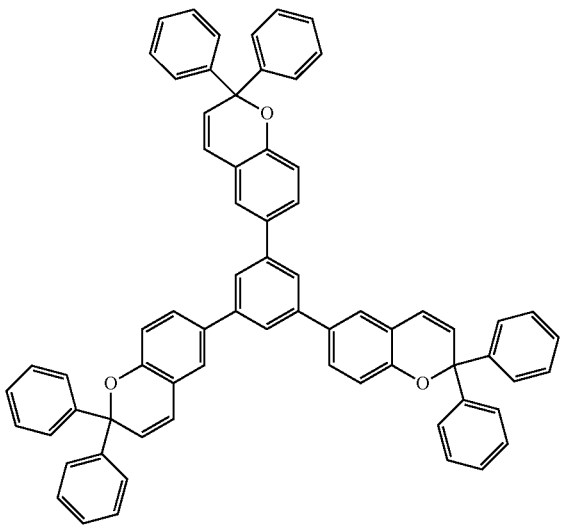

(A-1)

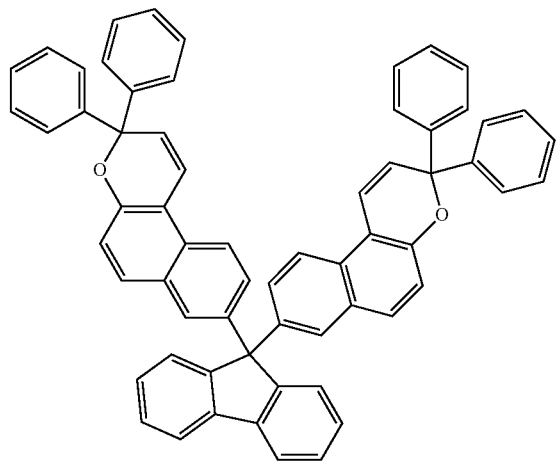

(A-2)

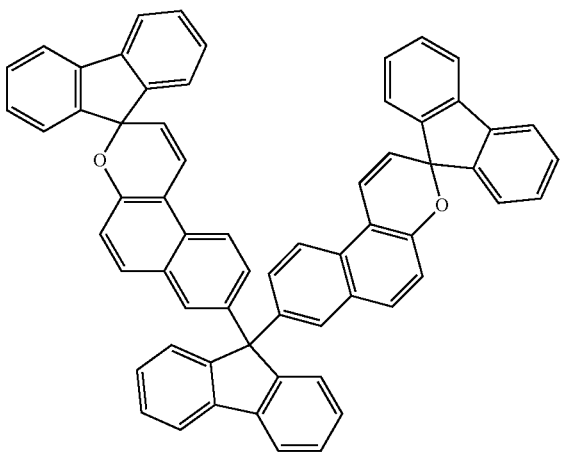

(A-3)

-continued (A-4)

(A-5)

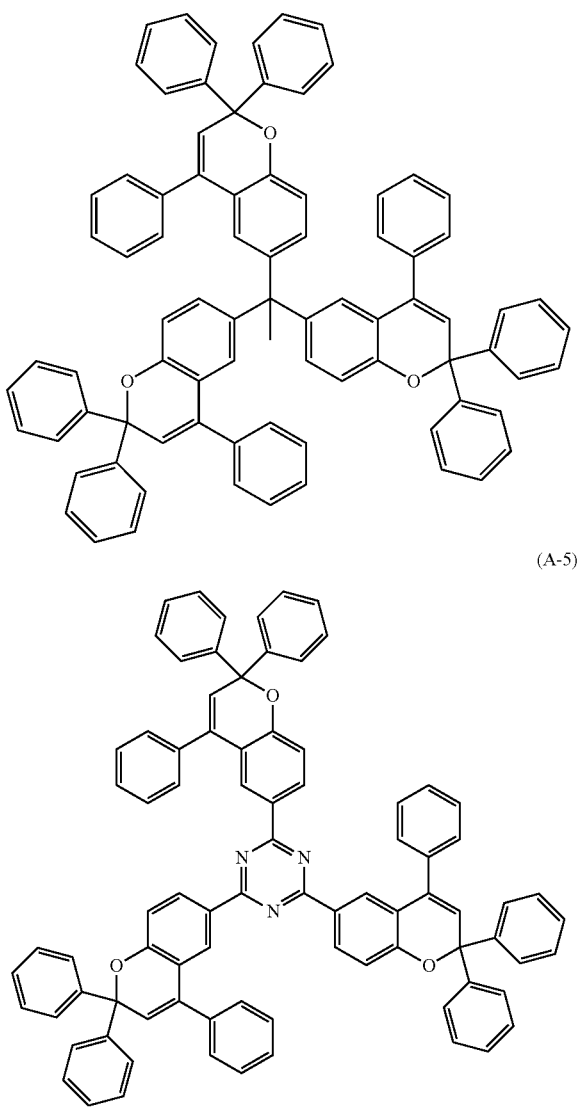

Example 1-1

To a 1,000-mL three-neck flask equipped with a thermometer, a condenser and a magnetic stirrer were added 40 g of p-hydroxy acetophenone and 400 g of ethanol in a nitrogen atmosphere, and dissolution was attained at room temperature. The solution thus obtained was cooled to 0° C., and then 249.6 g of silicon tetrachloride was added dropwise thereto over 1 hour. After the dropwise addition, the resulting solution was heated to 40° C. to allow for a reaction for 16 hrs. After the completion of the reaction, the reaction solution was added to a large quantity of water, and then 120 g of methyl isobutyl ketone was added thereto to permit extraction. The organic layer thus obtained was washed twice with water, and then charged into 600 g of hexane to permit reprecipitation. The precipitate thus obtained was filtered, recrystallized with N,N-dimethylacetamide, and then dried under reduced pressure at 60° C. to give a compound represented by the following formula (a-1) (amount: 24.0 g; yield: 69.2%).

(a-1)

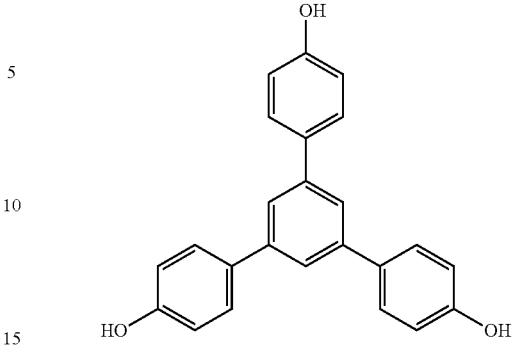

To a 1,000-mL three-neck flask equipped with a thermometer, a condenser and a magnetic stirrer were added 10 g of the compound (a-1), 255 g of dichloroethane, 35.9 g of trimethyl orthoformate and 26.4 g of 1,1-diphenyl-2-propyne-1-ol in a nitrogen atmosphere, and dissolution was attained at 80° C. To the resulting solution, 4.25 g of pyridinium p-toluenesulfonate was added and then a reaction was allowed at 80° C. for 16 hrs. After the completion of the reaction, the reaction solution was washed twice with water, and an organic layer thus obtained was concentrated to 108 g. The concentrate was charged into 540 g of methanol to permit reprecipitation. The precipitate thus obtained was dried under reduced pressure at 60° C. to give the compound (A-1) (amount: 16.1 g; yield: 61.7%).

Example 1-2

To a 1,000-mL three-neck flask equipped with a thermometer, a condenser and a magnetic stirrer were added 10 g of bisnaphthol fluorene, 239 g of dichloroethane, 14.1 g of trimethyl orthoformate and 13.9 g of 1,1-diphenyl-2-propyne-1-ol in a nitrogen atmosphere, and dissolution was attained at 80° C. To the resulting solution, 3.35 g of pyridinium p-toluenesulfonate was added and then a reaction was allowed at 80° C. for 16 hrs. After the completion of the reaction, the reaction solution was washed twice with water, and an organic layer thus obtained was concentrated to 72 g. The concentrate was charged into 360 g of methanol to permit reprecipitation. The precipitate thus obtained was dried under reduced pressure at 60° C. to give the compound (A-2) (amount: 14.8 g; yield: 80.2%).

Example 1-3

The compound (A-3) was obtained by a similar operation to that of Example 1-2 except that 9-ethynyl-9-fluorenol was used in place of 1,1-diphenyl-2-propyne-1-ol in an equimolar ratio (amount: 13.2 g; yield: 71.9%).

Example 1-4

To a 1,000-mL three-neck flask equipped with a thermometer, a condenser and a magnetic stirrer were added 10 g of 1,1,1-tris(4-hydroxyphenyl)ethane, 294 g of chlorobenzene and 41.8 g of 1,1,3-triphenyl-2-propyne-1-ol in a nitrogen atmosphere, and dissolution was attained at 50° C. To the resulting solution, 3.73 g of p-toluenesulfonic acid monohydrate was added and then a reaction was allowed at 50° C. for 8 hrs. After the completion of the reaction, the reaction solution was washed twice with water, and an organic layer thus obtained was concentrated to 128 g. The concentrate was charged into 640 g of methanol to permit reprecipitation. The precipitate thus obtained was dried under reduced pressure at 60° C. to give the compound (A-4) (amount: 26.6 g; yield: 73.7%).

Example 1-5

To a 1,000-mL three-neck flask equipped with a thermometer, a condenser and a magnetic stirrer were added 40 g of 4-cyanophenol and 400 g of dichloromethane in a nitrogen atmosphere, and dissolution was attained at room temperature. The solution thus obtained was cooled to 0° C., and 252.0 g of trifluoromethanesulfonate was added dropwise thereto over 1 hour. After the dropwise addition, the resulting solution was heated to 30° C. to allow for a reaction for 24 hrs. After the completion of the reaction, the reaction solution was neutralized with a 1 mass % aqueous solution of ammonium hydroxide, and the precipitate generated was collected by filtration. The solid thus collected was recrystallized with methyl ethyl ketone, and then dried under reduced pressure at 60° C. to give a compound represented by the following formula (a-5) (amount: 31.5 g; yield: 78.8%).

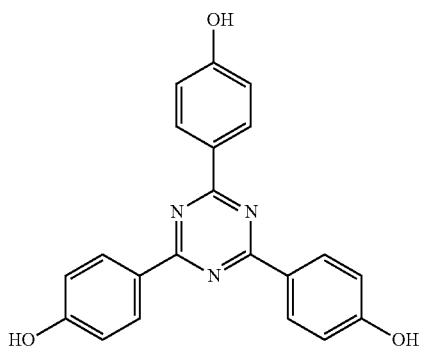

(a-5)

To a 1,000-mL three-neck flask equipped with a thermometer, a condenser and a magnetic stirrer were added 10 g of the compound (a-5), 255 g of dichloroethane, 35.9 g of trimethyl orthoformate and 26.4 g of 1,1-diphenyl-2-propyne-1-ol in a nitrogen atmosphere, and dissolution was attained at 80° C. To the resulting solution, 4.25 g of pyridinium p-toluenesulfonate was added and then a reaction was allowed at 80° C. for 16 hrs. After the completion of the reaction, the reaction solution was washed twice with water, and an organic layer thus obtained was concentrated to 108 g. The concentrate was charged into 540 g of methanol to permit reprecipitation. The precipitate thus obtained was dried under reduced pressure at 60° C. to give the compound (A-5) (amount: 17.3 g; yield: 66.6%).

Synthesis Example 1-1

To a reactor equipped with a condenser, a thermometer and a stirrer were added 100 parts by mass of 2,7-dihydroxy naphthalene, 100 parts by mass of propylene glycol monomethyl ether acetate, and 50 parts by mass of paraformaldehyde. After adding 2 parts by mass of oxalic acid thereto, the resulting solution was heated to 120° C. with dehydration to allow for a reaction for 5 hrs. Accordingly, a compound (b-1) which is a polymer having a structural unit represented by the following formula (b-1) was obtained. The obtained compound (b-1) had an Mw of 3,000.

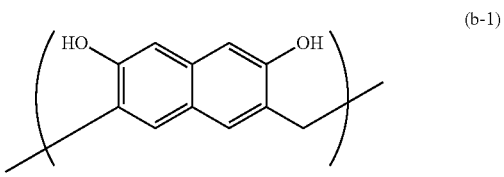

(b-1)

Preparation of Composition for Film Formation

The solvent (B), the acid generating agent (C) and the crosslinking agent (D) used in preparation of the composition for film formation are shown below.

(B) Solvent

B-1: Propylene Glycol Monomethyl Ether Acetate (C) Acid Generating Agent

C-1: bis(4-t-butylphenyl)iodonium nonafluoro-n-butanesulfonate (a Compound Represented by the Following Formula (C-1))

C-2: triethylammonium nonafluoro-n-butanesulfonate (a Compound Represented by the Following Formula (C-2))

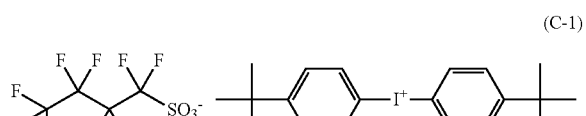

(C-1)

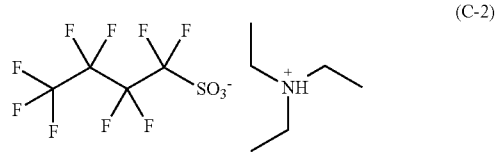

(C-2)

(D) Crosslinking Agent

D-1: 1,3,4,6-tetrakis(methoxymethyl)glycoluril (a Compound Represented by the Following Formula (D-1))

D-2:

4,4'-(1-(4-(1-(4-hydroxy-3,5-bis(methoxymethyl) phenyl)-1-methylethyl)phenyl)ethylidene)bis(2,6-bis (methoxymethyl)phenol (a Compound Represented by the Following Formula (D-2))

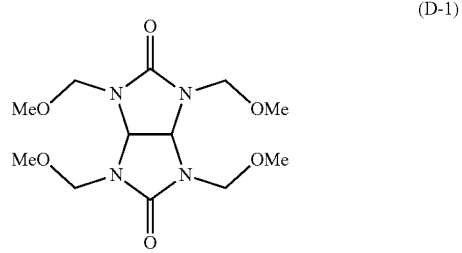

(D-1)

-continued

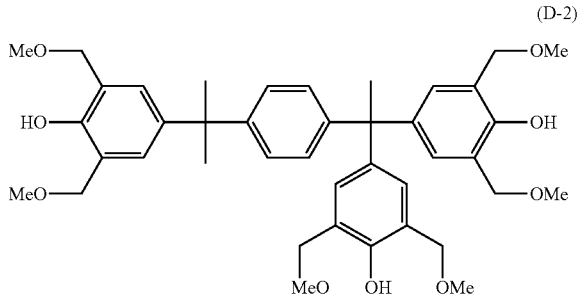

(D-2)

Example 2-1

Ten parts by mass of (A-1) as the compound (A) were dissolved in 90 parts by mass of (B-1) as the solvent (B). The obtained solution was filtered through a membrane filter having a pore size of 0.1 μm to prepare a composition for film formation (J-1).

Examples 2-2 to 2-7 and Comparative Example 2-1

Compositions for film formation (J-2) to (J-7) and (CJ-1) were prepared by a similar operation to that of Example 2-1 except that the type and the content of each component used were as shown in Table 1 below. In Table 1, "-" indicates that the corresponding component was not used.

Solvent Resistance

The substrate provided with the resist underlayer film obtained as described above was immersed in cyclohexanone (at room temperature) for 1 min. The average film thickness was measured before and after the immersion. The average thickness of the resist underlayer film before the immersion was designated as $X_0$ and the average thickness of the resist underlayer film after the immersion was designated as X, and the absolute value of a numerical value determined according to $(X-X_0)\times 100/X_0$ was calculated and designated as the rate of change of film thickness (%). The solvent resistance was evaluated to be: "A" (favorable) in a case in which the rate of change of film thickness was less than 1%; "B" (somewhat favorable) in a case in which the rate of change of film thickness was no less than 1% and less than 5%; and "C" (unfavorable) in a case in which the rate of change of film thickness was no less than 5%.

Etching Resistance

The resist underlayer film of the substrate provided with the resist underlayer film obtained as described above was treated in an etching apparatus ("TACTRAS" available from Tokyo Electron Limited) under conditions involving: $CF_4$/Ar=110/440 sccm, PRESS.=30 MT, HF RF=500 W, LF RF=3,000 W, DCS=−150 V, RDC=50%, and 30 sec. An etching rate (nm/min) was calculated based on the average thickness of the resist underlayer film before the treatment and the average thickness of the resist underlayer film after the treatment, and the ratio of the etching rate of the resist underlayer film of each Example to that of Comparative Example 3-1 was calculated as a standard for etching

TABLE 1

| | Composition for film formation | (A) Compound | | (B) Solvent | | (C) Acid-generating agent | | (D) Crosslinking agent | |
|---|---|---|---|---|---|---|---|---|---|
| | | Type | Content (parts by mass) | Type | Content (parts by mass) | Type | Content (parts by mass) | Type | Content (parts by mass) |
| Example 2-1 | J-1 | A-1 | 10 | B-1 | 90 | — | — | — | — |
| Example 2-2 | J-2 | A-2 | 10 | B-1 | 90 | — | — | — | — |
| Example 2-3 | J-3 | A-3 | 10 | B-1 | 90 | — | — | — | — |
| Example 2-4 | J-4 | A-4 | 10 | B-1 | 90 | — | — | — | — |
| Example 2-5 | J-5 | A-5 | 10 | B-1 | 90 | — | — | — | — |
| Example 2-6 | J-6 | A-1 | 10 | B-1 | 90 | C-1 | 0.5 | D-2 | 1 |
| Example 2-7 | J-7 | A-1 | 10 | B-1 | 90 | C-2 | 0.5 | D-1 | 1 |
| Comparative Example 2-1 | CJ-1 | b-1 | 10 | B-1 | 90 | — | — | — | — |

Formation of Resist Underlayer Film

Examples 3-1 to 3-7 and Comparative Example 3-1

The compositions for film formation prepared as described above were each applied on a silicon wafer substrate by way of a spin-coating procedure. Thereafter, heating (baking) was carried out at the heating temperature CC) for the heating time period (sec) shown in Table 2 below in an ambient air atmosphere to form a resist underlayer film having a thickness of 200 nm, whereby substrates having the resist underlayer film formed thereon were obtained. In Table 2, "-" indicates that Comparative Example 3-1 serves as a standard for etching resistance evaluation.

Evaluations

For the compositions for film formation and the substrates with a resist underlayer film obtained as described above, the following evaluations were each made according to the following procedures. The results of the evaluations are shown in Table 2 below.

resistance evaluation. The etching resistance was evaluated to be: "A" (extremely favorable) in a case in which the ratio was no less than 0.95 and less than 0.98; "B" (favorable) in a case in which the ratio was no less than 0.98 and less than 1.00; and "C" (unfavorable) in a case in which the ratio was no less than 1.00.

Flatness

Each of the prepared compositions for film formation was applied by a spin-coating procedure using a spin coater ("CLEAN TRACK ACT-12" available from Tokyo Electron Limited), on a silicon substrate provided with a trench pattern having a depth of 100 nm and a groove width of 10 μm formed thereon. The rotational speed for the spin coating was the same as that in the case of forming the resist underlayer film having the average thickness of 200 nm in the "Formation of Resist Underlayer Film" described above. Subsequently, the resulting substrate was heated (baked) at 250° C. for 60 sec in an ambient air atmosphere to form a resist underlayer film that covers the silicon substrate.

The cross-sectional shape of the silicon substrate covered with the resist underlayer film was observed by using a scanning electron microscope ("S-4800" available from Hitachi High-Technologies Corporation), and the difference (ΔFT) between the height at the center portion of the trench pattern of the resist underlayer film and the height at a position 5 μm away from the edge of the trench pattern, at which no trench pattern was provided, was defined as a marker of the flatness. The flatness was evaluated to be "A" (extremely favorable) in the case of ΔFT being less than 20 nm, "B" (favorable) in the case of ΔFT being no less than 20 nm and less than 40 nm, and "C" (unfavorable) in the case of ΔFT being no less than 40 nm.

Heat Resistance

The composition for film formation prepared as described above was spin-coated on a silicon wafer having a diameter of 8 inches to obtain a substrate provided with a resist underlayer film. A powder was collected from the substrate provided with the resist underlayer film, and then the powder was heated in a TG-DTA apparatus ("TG-DTA2000SR" available from NETZSCH) in a nitrogen atmosphere with a rate of temperature rise of 10° C./min. The mass loss rate (%) after the heating was defined as a marker of heat resistance. The smaller value of the heat resistance indicates that the resist underlayer film is more favorable, i.e., more superior in heat resistance, as there are less sublimated matter and resist underlayer film degradation products generated during the heating of the resist underlayer film. The heat resistance was evaluated to be: "A" (extremely favorable) in a case in which the mass loss rate was less than 5%; "B" (favorable) in a case in which the mass loss rate was no less than 5% and less than 10%; and "C" (unfavorable) in a case in which the mass loss rate was no less than 10%.

TABLE 2

| | Composition for film formation | Heating temperature/ Heating time period for film formation (° C./sec) | Solvent resistance | Etching resistance | Flatness | Heat resistance |
|---|---|---|---|---|---|---|
| Example 3-1 | J-1 | 400/60 | A | A | A | A |
| Example 3-2 | J-2 | 400/60 | A | A | B | A |
| Example 3-3 | J-3 | 400/60 | A | A | B | A |
| Example 3-4 | J-4 | 400/60 | A | A | B | A |
| Example 3-5 | J-5 | 400/60 | A | A | A | A |
| Example 3-6 | J-6 | 250/60 | A | A | A | B |
| Example 3-7 | J-7 | 250/60 | A | A | A | B |
| Comparative Example 3-1 | CJ-1 | 250/60 | C | — | C | C |

As is clear from the results shown in Table 2, the films formed from the compositions for film formation of Examples were superior in flatness, solvent resistance, etching resistance and heat resistance. To the contrary, the film formed from the composition for film formation of Comparative Example was inferior in flatness and heat resistance, and exhibited poor performances in solvent resistance and etching resistance.

The composition for film formation according to the embodiment of the present invention is capable of forming a film that is superior in flatness, solvent resistance, etching resistance and heat resistance. The film according to the another embodiment of the present invention is superior in flatness, solvent resistance, etching resistance and heat resistance. The resist underlayer film-forming method of the yet another embodiment of the present invention enables formation of a resist underlayer film superior in flatness. The method for producing a patterned substrate according to the still another embodiment of the present invention enables a substrate having a superior pattern configuration to be obtained using the superior resist underlayer film thus formed. The compound according to the still yet another embodiment of the present invention can be suitably used as a component for the composition for film formation. Therefore, these can be suitably used in manufacture of semiconductor devices, and the like in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A composition for film formation comprising:
   an aromatic ring-containing compound represented by formula (i); and
   a solvent:

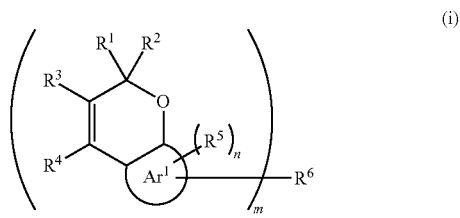

wherein in the formula (i), $R^1$ and $R^2$ each independently represent a monovalent organic group having 1 to 20 carbon atoms, $R^3$ and $R^4$ each independently represent a hydrogen atom or a monovalent organic group having 1 to 20 carbon atoms, and optionally at least part of $R^1$ to $R^4$ taken together represent a cyclic structure having 3 to 20 ring atoms together with the carbon atom or a carbon chain to which the at least part of $R^1$ to $R^4$ bond, $Ar^1$ represents a group obtained by removing (n+3) hydrogen atoms from an aromatic ring of an arene having 6 to 20 carbon atoms, n is an integer of 0 to 9, m is an integer of 2 to 6, $R^5$ represents a hydroxy group, a halogen atom, a nitro group, or a monovalent organic group having 1 to 20 carbon atoms, and optionally in a case in which $R^5$ is present in a plurality of number, two or more of the plurality of $R^5$s taken together represent a cyclic structure having 6 to 20 ring atoms together with an atomic chain to which the two or more of the plurality of $R^5$s bond, a plurality of $R^1$s are identical or different, a plurality of $R^2$s are identical or different, a plurality of $R^3$s are identical or different, a plurality of $R^4$s are identical or different, and in the case in which $R^5$ is present in a plurality of number, the plurality of $R^5$s are identical or different, and $R^6$ represents at least one selected from the group consisting of a group represented by formula (2-1), a group represented by formula (2-2), a group represented by formula (2-3), a group represented by formula (2-4), and a group represented by formula (2-5):

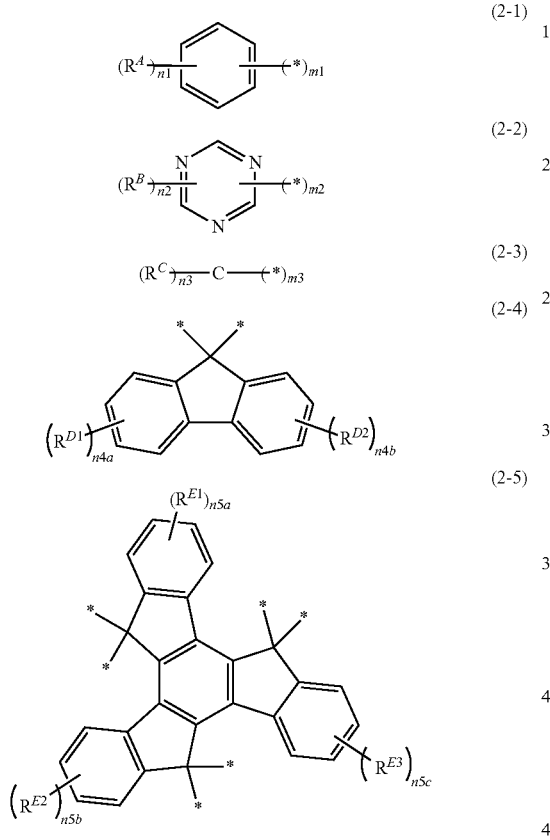

wherein in the formulae (2-1) to (2-5), * denotes a binding site to the carbon atom in the aromatic ring of $Ar^1$ in the formula (i), in the formula (2-1), $R^A$ represents a hydroxy group, a halogen atom, a nitro group, or a monovalent organic group having 1 to 20 carbon atoms; n1 is an integer of 0 to 4, wherein in a case in which n1 is 2 or greater, a plurality of $R^A$s are identical or different; and m1 is an integer of 2 to 6, wherein n1+m1≤6, in the formula (2-2), $R^B$ represents a hydroxy group, a halogen atom, a nitro group, or a monovalent organic group having 1 to 20 carbon atoms; n2 is an integer of 0 or 1; and m2 is an integer of 2 or 3, wherein n2+m2≤3, in the formula (2-3), $R^C$ represents a hydrogen atom, a hydroxy group, a halogen atom, a nitro group, or a monovalent organic group having 1 to 20 carbon atoms; n3 is an integer of 0 to 2, wherein in a case in which n3 is 2, a plurality of $R^C$s are identical or different; and m3 is an integer of 2 to 4, wherein n3+m3=4, in the formula (2-4), $R^{D1}$ and $R^{D2}$ each independently represent a hydroxy group, a halogen atom, a nitro group, or a monovalent organic group having 1 to 20 carbon atoms; and n4a and n4b are each independently an integer of 0 to 4, wherein in a case in which n4a is 2 or greater, a plurality of $R^{D1}$s are identical or different, and in a case in which n4b is 2 or greater, a plurality of $R^{D2}$s are identical or different, and in the formula (2-5), $R^{E1}$ to $R^{E3}$ each independently represent a hydroxy group, a halogen atom, a nitro group, or a monovalent organic group having 1 to 20 carbon atoms; and n5a, n5b and n5c are each independently an integer of 0 to 4, wherein in a case in which n5a is 2 or greater, a plurality of $R^{E1}$s are identical or different, in a case in which n5b is 2 or greater, a plurality of $R^{E2}$s are identical or different, and in a case in which n5c is 2 or greater, a plurality of $R^{E3}$s are identical or different.

2. The composition for film formation according to claim 1, wherein the aromatic ring-containing compound has a molecular weight of no less than 300 and no greater than 3,000.

3. The composition for film formation according to claim 1, wherein $R^1$ and $R^2$ in the formula (i) each independently represent a substituted or unsubstituted aryl group or a substituted or unsubstituted heteroaryl group.

4. The composition for film formation according to claim 1, wherein $R^3$ in the formula (i) represents a hydrogen atom.

5. The composition for film formation according to claim 1, wherein the arene which $Ar^1$ in the formula (i) is derived from is benzene or naphthalene.

6. The composition for film formation according to claim 1, wherein a content of the compound in the composition is no less than 1% by mass and no greater than 50% by mass.

7. The composition for film formation according to claim 1, wherein the composition is suitable for formation of a resist underlayer film.

8. A resist underlayer film-forming method comprising:
applying the composition for film formation according to claim 1 directly or indirectly on an upper face side of a substrate to form a film on the upper face side of the substrate; and
heating the film to form a resist underlayer film.

9. A compound represented by formula (i):

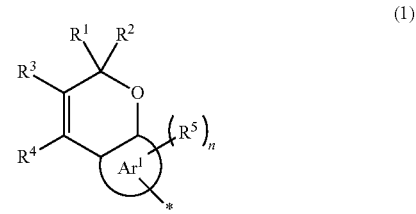

wherein in the formula (i),
$R^1$ to and $R^2$ each independently represent a monovalent organic group having 1 to 20 carbon atoms, $R^3$ and $R^4$ each independently represent a hydrogen atom, or a monovalent organic group having 1 to 20 carbon atoms, and optionally at least part of $R^1$ to $R^4$ taken together represent a cyclic structure having 3 to 20 ring atoms together with the carbon atom or a carbon chain to which the at least part of $R^1$ to $R^4$ bond, Ar¹ represents a group obtained by removing (n+3) hydrogen atoms from an aromatic ring of an arene having 6 to 20 carbon atoms, n is an integer of 0 to 9, m is an integer of 2 to 6, $R^5$ represents a hydroxy group, a halogen atom, a nitro group, or a monovalent organic group having 1 to 20 carbon atoms, and optionally in a case in which $R^5$ is present in a plurality of number, two or more of the plurality of $R^5$s taken together represent a cyclic structure having 6 to 20 ring atoms together with an atomic chain to which the two or more of the plurality of $R^5$s bond, a plurality of $R^1$s are identical or different, a plurality of $R^2$s are identical or different, a plurality of $R^3$s are identical or different, a plurality of $R^4$s are identical or different, and in the case in which $R^5$ is present in a plurality of number, the plurality of $R^5$s are identical or different, and $R^6$ represents at least one selected from the group consisting of a group represented by formula (2-1), a group represented by formula (2-2), a group represented by formula (2-3), a group represented by formula (2-4), and a group represented by formula (2-5):

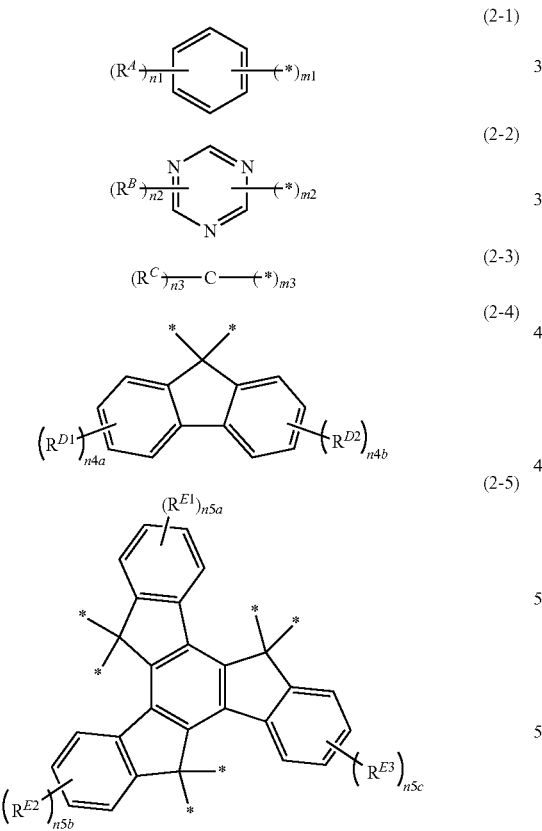

wherein in the formulae (2-1) to (2-5), * denotes a binding site to the carbon atom in the aromatic ring of Ar¹ in the formula (i), in the formula (2-1), $R^A$ represents a hydroxy group, a halogen atom, a nitro group, or a monovalent organic group having 1 to 20 carbon atoms; n1 is an integer of 0 to 4, wherein in a case in which n1 is 2 or greater, a plurality of $R^A$s are identical or different; and m1 is an integer of 2 to 6, wherein n1+m1≤6, in the formula (2-2), $R^B$ represents a hydroxy group, a halogen atom, a nitro group, or a monovalent organic group having 1 to 20 carbon atoms; n2 is an integer of 0 or 1; and m2 is an integer of 2 or 3, wherein n2+m2≤3, in the formula (2-3), $R^C$ represents a hydrogen atom, a hydroxy group, a halogen atom, a nitro group, or a monovalent organic group having 1 to 20 carbon atoms; n3 is an integer of 0 to 2, wherein in a case in which n3 is 2, a plurality of $R^C$s are identical or different; and m3 is an integer of 2 to 4, wherein n3+m3=4, in the formula (2-4), $R^{D1}$ and $R^{D2}$ each independently represent a hydroxy group, a halogen atom, a nitro group, or a monovalent organic group having 1 to 20 carbon atoms; and n4a and n4b are each independently an integer of 0 to 4, wherein in a case in which n4a is 2 or greater, a plurality of $R^{D1}$s are identical or different, and in a case in which n4b is 2 or greater, a plurality of $R^{D2}$s are identical or different, and in the formula (2-5), $R^{E1}$ to $R^{E3}$ each independently represent a hydroxy group, a halogen atom, a nitro group, or a monovalent organic group having 1 to 20 carbon atoms; and n5a, n5b and n5c are each independently an integer of 0 to 4, wherein in a case in which n5a is 2 or greater, a plurality of $R^{E1}$s are identical or different, in a case in which n5b is 2 or greater, a plurality of $R^{E2}$s are identical or different, and in a case in which n5c is 2 or greater, a plurality of $R^{E3}$s are identical or different.

10. The compound according to claim 9, wherein the compound has a molecular weight of no less than 300 and no greater than 3,000.

11. The composition for film formation according to claim 1, wherein the aromatic ring-containing compound has a molecular weight of no less than 300 and no greater than 3,000, $R^1$ and $R^2$ in the formula (i) each independently represent a substituted or unsubstituted aryl group or a substituted or unsubstituted heteroaryl group, $R^3$ in the formula (i) represents a hydrogen atom, and the arene which Ar¹ in the formula (i) is derived from is benzene or naphthalene.

12. A production method of a patterned substrate comprising:
applying the composition for film formation according to claim 1 directly or indirectly on an upper face side of a substrate to form a film on the upper face side of the substrate;
heating the film to form a resist underlayer film;
forming a resist pattern directly or indirectly on an upper face side of the resist underlayer film; and
etching the substrate using the resist pattern as a mask.

13. The production method of a patterned substrate according to claim 12, wherein the aromatic ring-containing compound has a molecular weight of no less than 300 and no greater than 3,000.

14. The production method of a patterned substrate according to claim 12, wherein $R^1$ and $R^2$ in the formula (i) each independently represent a substituted or unsubstituted aryl group or a substituted or unsubstituted heteroaryl group.

15. The production method of a patterned substrate according to claim 12, wherein $R^3$ in the formula (i) represents a hydrogen atom.

16. The production method of a patterned substrate according to claim 12, wherein the arene which $Ar^1$ in the formula (i) is derived from is benzene or naphthalene.

17. The compound according to claim 9, wherein $R^1$ and $R^2$ in the formula (i) each independently represent a substituted or unsubstituted aryl group or a substituted or unsubstituted heteroaryl group.

18. The compound according to claim 9, wherein $R^3$ in the formula (i) represents a hydrogen atom.

19. The compound according to claim 9, wherein the arene which $Ar^1$ in the formula (i) is derived from is benzene or naphthalene.

\* \* \* \* \*

UNITED STATES PATENT AND TRADEMARK OFFICE
CERTIFICATE OF CORRECTION

PATENT NO. : 11,003,079 B2  
APPLICATION NO. : 16/205502  
DATED : May 11, 2021  
INVENTOR(S) : Naoya Nosaka et al.

Page 1 of 1

It is certified that error appears in the above-identified patent and that said Letters Patent is hereby corrected as shown below:

In the Claims

Column 36 Lines 50-55:
The image of the formula in Claim 9:

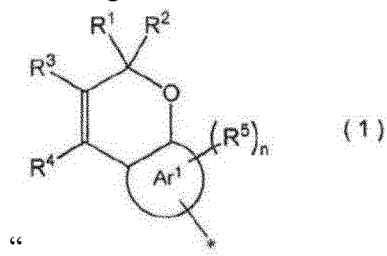

Should appear as:

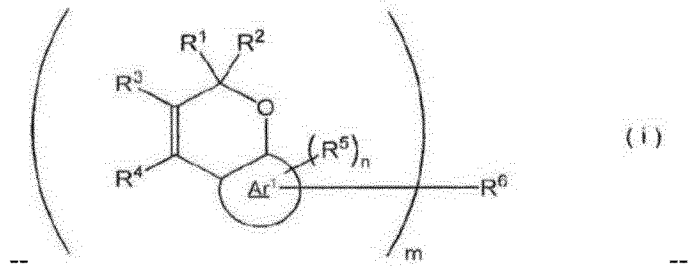

Signed and Sealed this  
Thirteenth Day of July, 2021

Drew Hirshfeld  
*Performing the Functions and Duties of the  
Under Secretary of Commerce for Intellectual Property and  
Director of the United States Patent and Trademark Office*